United States Patent [19]
Rothstein et al.

[11] Patent Number: 5,789,188
[45] Date of Patent: Aug. 4, 1998

[54] TETRACYCLINE-EFFLUX PUMP INHIBITOR SCREENING METHODS

[75] Inventors: David Michael Rothstein, Pomona; Gordon Gerald Guay, Harriman, both of N.Y.

[73] Assignee: American Cyanamid Company, Madison, N.J.

[21] Appl. No.: 644,931

[22] Filed: May 13, 1996

Related U.S. Application Data

[63] Continuation of Ser. No. 218,875, Mar. 25, 1994, abandoned, which is a continuation of Ser. No. 803,634, Dec. 6, 1991, abandoned.

[51] Int. Cl.$^6$ .............................. C12Q 1/02; C12N 1/21; C12N 1/00
[52] U.S. Cl. ............................ 435/29; 435/4; 435/252.3
[58] Field of Search ........................... 435/29, 32, 252.1, 435/252.3, 252.33, 4

[56] References Cited

U.S. PATENT DOCUMENTS

| | | | |
|---|---|---|---|
| 4,806,529 | 2/1989 | Levy ........................................ | 514/154 |
| 4,911,924 | 3/1990 | Griffith et al. ........................... | 424/114 |
| 5,001,230 | 3/1991 | Brown et al. ............................ | 536/23.5 |

OTHER PUBLICATIONS

McMurray, L.M. et al., "Active efflux of tetracycline encoded by four genetically different tetracycline resistance elements in *Escherichia coli*", Proc. Natl. Acad. Sci., 77:3974–3977, 1980.

Mojumdar, M. and S.A. Khar, Characterization of the tetracycline resistance gene of plasmid pT181 of *Staphylococcus aureus*. J. Bacteriol. 170:5522–5528, 1988.

Coleman, D.C. and T.J. Foster, "Analysis of the reduction in expression of tetracycline resistance determined by transposon Tn10 in the multicopy state", Mol. Gen. Genet. 182:171–177, 1981.

Moyed, J.S., et al., "Multicopy Tn10 tet plasmids confer sensitivity to induction of tat gene expression", J. Bacteriol., 155:549–556, 1983.

Bertrand, K.P., et al., "Overlapping divergent promoters control expression of Tn10 tetracycline resistance", Gene, 23:149–156, 1983.

Hillen, W. et al., "Control of expression of the Tn10–encoded tetracycline resistance operon II. Interaction of RNA polymerase and TET repressor with the tet operon regulatory region", J. Mol. Biol., 172:185–201, 1983.

Eckert, B. et al., "Overproduction of Transposon Tn10–Encoded Tetracycline Protein Results in Cell Death and Loss of Membrane Potential", J. Bact. 171:3557–3559, 1989.

Bertrand, K.P. et al., "Construction of a single–cop promoter vector and its use in analysis of regulation of the transposon Tn10 tetracycline resistance determinant", J. Bacteriol., 158:910–919, 1984.

Miller, J.H., "Experiments in Molecular Genatics", Cold Spring Harbor Laboratories, Cold Spring Harbor, N.Y.

Chopra, I. et al., "Sensitive biological detection method for tetracycline using a tetA–lacZ fusion system", Antimicrob. Agents Chemoth., 34:111–116, 1990.

Rothstein, D.M. et al., "Regulation of expression from the glnA promoter of *Escherichia coli* in the absence of glutamine synthetase", Proc. Nat. Acad. Sci. 77:7372–7376, 1980.

Hershey, A.D. (ed.), "The Bacteriophage Lamdda", Cold Spring Harbor Laboratories, Cold Spring Harbor, N.Y., 1971.

Kunkel, T.A. et al., "Rapid and efficient site–specific mutagenesis without phenotypic selection", Methods Enzymology, 154:367, 1987.

Davis, R.W. et al., "Advanced Bacterial Genetics", Cols Spring Harbor Laboratory, Cold Spring Harbor, N.Y., 1980.

Osburne, M.O., "In vivo inhibition of bacterial DNA gyrase by cinodinne, a glycocinnamoylspermidine antibiotic", Antimicrobial Agents and Chemotherapy, 34:1450–1452, 1990.

Smith, L.D. et al., "Mutations in the Tn10 repressor that interfere with induction, location of the tetracycline–binding domain", J. Mol. Biol., 203:929–959, 1988.

Bochner, B.R. et al., "Positive selection for loss of tetracycline resistance", J. Bacteriol. 143:926–933, 1980.

Schwyn, R. et al., "Universal chemical assay for the detection and determination of siderophores", Analytical Biochemistry, 160:47–56, 1987.

(List continued on next page.)

*Primary Examiner*—George C. Elliott
*Assistant Examiner*—Johnny F. Railey, II
*Attorney, Agent, or Firm*—Elizabeth M. Barnhard; Karen A. Lowney

[57] ABSTRACT

A method for detecting a tetracycline efflux pump inhibitor in the presence of tetracycline using a reporter gene system where the tetA promoter directs transcription of a reporter gene (lacZ) while the tetA is under the control of the tet repressor encoded by the tetR gene is described. The method uses a cell having a reporter gene system where the tetA promoter directs transcription of a reporter gene (lacZ) and an active efflux system in which relatively modest levels of the efflux protein encoded by the tetA gene are produced in a constitutive manner, i.e., not under the control of the tet repressor encoded by the tetR gene. Test samples which are inhibitors of the TetA efflux protein will allow accumulation of tetracycline inside the cells at levels which will induce expression of the tetA–lacZ transcriptional fusion to give a positive signal. A microorganism is also described which is refractory to induction by DNA damaging agents and comprises (1) an indicator gene fused to a tetA promoter, as a single- or low-copy number gene; (2) a tetR gene expressed at low levels, preferably at a level producing a sensitivity to 10 ng or less of tetracycline, and (3) a constitutive gene encoding a tetracycline efflux pump.

26 Claims, 10 Drawing Sheets

OTHER PUBLICATIONS

Gold, L. et al., "*Escherichia coli* and *Salmonella Typhimutium*: Cellular and Molecular Biology", F.C. Niedhard (ed.), American Society of Microbiology, Washington, D.C., vol. 2:1302–1307, 1987.

Dosch, D.C. et al., "Tetracycline Resistance Element of pBR322 Mediates Potassium Transport", J. Bacteriol. 160:1188–1190, 1984.

Rubin, R.A. and S. Levy, "Interdomain Hybrid Tet Proteins Confer Tetracycline Resistance Only When They are Derived from Closely Related Members of the tet Gene Family", J. Bacteriol., 172:2303–2312, 1990.

Bailey, J. E. (1991) Toward A Science of Metabolic Engineering. Science, vol. 252, pp. 1668–1675.

```
GTAAAGAGGTAAAATTGTTTAGTTTA    (WILD TYPE MC71)
       CG  CA                 (PT1813)
       CG  CT                 (PT1814)

Sal I

GTCGACATGTTTAGTTT          pGG57 (tetK ATG)

Sal I

GTCGACTTGTTTAGTTT          pGG71 (tetK TTG)
```

FIG. 2

| Plasmid | Construct | Amino Acid residues (tetK) |
|---------|-----------|----------------------------|
| pGG57 | pCBSal containing tetK (ATG start) | 431 |
| pGG76 | pACYC184 derivative containing lacI-tetK | 431 |
| pGG77 | ▲ KpnI/SpeI from pGG76 | 196 |
| pGG84 | ▲ EcoNI from pGG76 | 161 |

FIG. 4

TETRACYCLINE-EFFLUX PUMP INHIBITOR SCREENING METHODS

This is a continuation of application Ser. No. 08/218,875 filed on Mar. 25, 1994, now abandoned which is a continuation of application Ser. No. 07/803,634 filed on Dec. 6, 1991 now abandoned.

FIELD OF THE INVENTION

The present invention relates to microorganisms and assays useful in the detection of tetracyclines or tetracycline efflux pump inhibitors in a test sample.

BACKGROUND OF THE INVENTION

The use of microorganisms, particularly E. coli, to express foreign genes for protein production has been commonplace for many years. Since, in most cases, the purpose for using the microorganisms is to permit the production of large quantities of the protein for commercial purposes, it is usually desired to express the protein at the highest possible level. For this reason, most expression systems and the DNA constructs used therein, are specifically adapted for high level expression. However, there are situations in which low to moderate level expression is actually more desirable, or even essential. For example, overexpression of some genes is lethal. Also, in cases in which microorganisms are used as the basis for a screen to detect action of a drug against a particular gene product, a low level of expression of the protein provides for enhanced sensitivity. However, fine-tuning the level of expression is not a routine task.

As an example, it is desirable to achieve low to moderate levels of expression of the genes encoding tetracycline resistance in order to develop appropriate microorganisms for screening drugs that overcome tetracycline resistance. This resistance in the majority of microorganisms is the result of an energy-dependent efflux system (1). These efflux pumps have been analyzed in a variety of both Gram-negative and Gram-positive bacteria, and all have shown a similar secondary structure with multiple membrane spanning domains. Nonetheless, comparison of the amino acid sequence of the most common Gram-negative pump, as encoded by the tetA gene from transposon Tn10 of E. coli, and the tetK gene from Gram-positive Staphylococcus aureus shows little identity (2). However, since these two pumps perform similar functions, it would be useful to perform studies on the tetK gene encoding the tetracycline efflux pump of S. aureus in an E. coli host, given the ease of performing genetic manipulations and biochemical studies in this system. In addition, the use of isogenic strains allows better comparison of the two efflux pumps.

A problem exists, however, if the tetA or tetK genes are cloned into a standard strong expression vector, overexpression of the tetA gene from transposon Tn10 is lethal to E. coli, e.g., if this gene is induced in a multicopy plasmid (3, 4). In Gram-negative bacteria, regulation of the pump is mediated by the tetR gene product, a repressor, located adjacent to a common regulatory region for tetA and tetR (5, 6). Therefore, assuming expression of other genes encoding efflux pumps, such as tetK, could be achieved, it is also possible that full expression would also be lethal to E. coli.

Attempts to modify the Tn10 system to permit controlled expression of the tetA gene have been made. Eckert and Beck (7) have recently cloned and expressed tetA from transposon Tn10 on a multicopy plasmid in the absence of tetR, using a regulated inducible expression system. In this system when tetA is fully induced, the cells again die, perhaps due to the dissipation of the proton motive force (7); active efflux of tetracycline out of bacteria is energized by the entry of a proton into the cell, but full induction apparently leads to the loss of the proton gradient essential to the bacteria's survival. In the Eckert and Beck system, the tetA gene is regulated at the level of transcription using a regulatory region containing the strong tac promoter and the lacI gene (encoding the lactose repressor) and the lac operator site on the multi-copy plasmid pCB258. Expression of the tetA gene can be regulated using different concentrations of isopropyl-B-D-thiogalactopyranoside (IPTG).

Unfortunately, the Eckert and Beck system is unsuitable for the purpose of building an optimal screening organism for detection of inhibitors of the tetracycline efflux pump. First, restriction analysis of the plasmid pCB258 indicates that one of the two tetR operator sites of the tet regulatory region remain in the plasmid adjacent to the tetA coding region. Thus, the tetA gene is regulated both by the lac repressor as well as the tetracycline repressor, if both repressors are present in the cell. The presence of both repressors causes deleterious consequences in an expression system designed for use as a screening organism. Thus, although pCB258 does permit relatively weakened expression of the tetA gene, the level of tetracycline resistance is nonetheless too high for use in screening for pump inhibitors. Moreover, there is no convenient restriction site in the appropriate region to permit insertion of an alternate gene such as tetK.

In order to overcome these difficulties, the present invention provides DNA constructs, vectors and E. coli host cells which result in low to moderate levels of the tetracycline resistance. Such materials are particularly useful in creation of screening assays for inhibitors of tetracycline resistance.

Figure 1A:
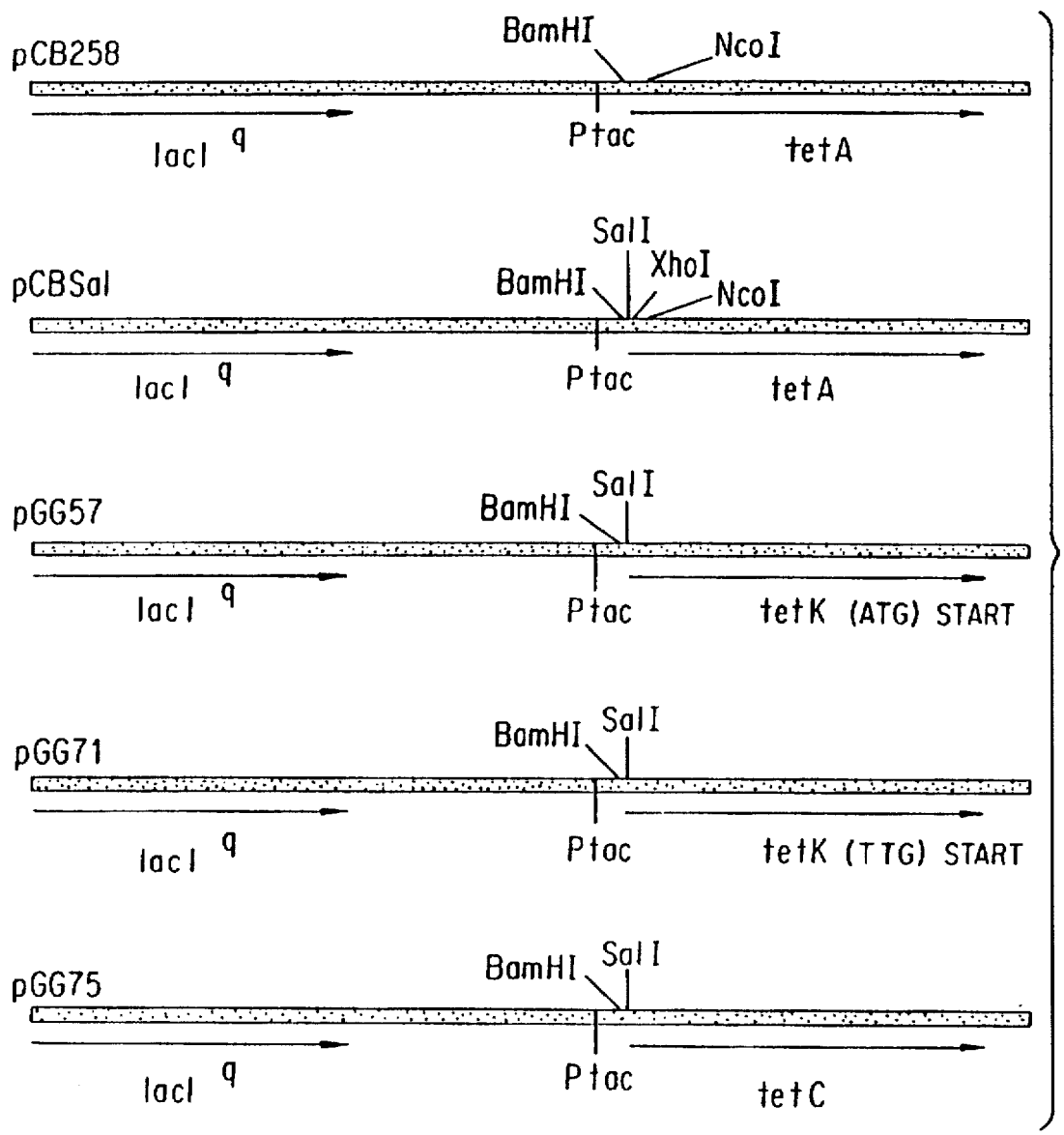
FIG. 1 (Panels A and B).

Panel A. A schematic representation of the parental plasmid (pCB258) and the four derivatives pCBSal, pGG57, pGG71 and pGG75. Plasmids pCBSal and pCB258 contain the tetA gene, encoding the tetracycline efflux pump from transposon Tn10 of E. coli. Restriction sites found around the start of transcription for tetA present in either pCBSal or pCB258 are depicted. Plasmid pCBSal is deleted for part of the tetracycline repressor operator site located in pCB258, and contains two additional restriction sites (SalI and XhoI). Plasmids pGG57 and pGG71 contain the tetK gene, encoding the tetracycline efflux pump derived from Staphylococcus aureus, present in a 2.0 Kb SalI/HindIII fragment isolated M13 bacteriophage designated GG1 and GG2 respectively. GG1 and GG2 are both generated by oligonucleotide-mediated site-directed mutagenesis of M13 bacteriophage MC71. pGG75 contains a tetC gene, encoding the tetracycline efflux pump derived from pBR322, with a SalI restriction site introduced 5' to the ATG of tetC using Polymerase Chain Reaction. Regulated expression of tetC to high levels of tetracycline resistance involves an uncharacterized regulatory mutation shown by DNA sequence analysis to reside outside of the tetC coding region. The lacI gene encodes the lac repressor which regulates expression of genes under the control of the tac promoter using IPTG.

Panel B. The top DNA sequence (SEQ ID NO:1) is from transposon Tn10 between tetR, encoding the tetracycline repressor, and tetA, encoding the tetracycline efflux pump. The two operator sites found in Tn10 (SEQ ID NO:1) are underlined and the location of the BamHI restriction site is inferred to be present between the two operator sites, from restriction analysis.

Although pCBSal (SEQ ID NO:2) contains two unique restriction sites, these changes do not result in alterations of the tetA encoded protein at the amino acid level. The only difference between the two tetK constructs is at the start of translation. The plasmid pGG57 (SEQ ID NO:3) contains an ATG start codon (underlined) while pGG71 (SEQ ID NO:4) contains a TTG start codon (underlined). All start codons for each construct are depicted by an arrow.

FIG. 2. Site-directed mutagenesis near the start codon of tetK. The DNA region near the start codon of tetK in the bacteriophage MC71 which was altered using oligonucleotide-mediated site-directed mutagenesis is shown (SEQ ID NO:5). Oligonucleotide-mediated site-directed mutagenesis requires: (1) a single stranded DNA template one wishes to mutagenize and (2) a short (20–40 bp) complementary oligonucleotide containing within it the desired changes one wishes to introduce into the DNA fragment. The oligonucleotide is allowed to anneal to the complementary single stranded template. Once annealed, the 3' OH group of the oligonucleotide serves as a primer for DNA polymerase which is added and results in production of a double stranded product. One of the two strands now contains the alterations introduced by the oligonucleotide primer.

This technique was used with two different oligonucleotide primers (PT1813 (SEQ ID NO:6) and PT1814 (SEQ ID NO:7)). The changes in DNA sequence at or near the natural tetK start site are depicted. Both of these oligonucleotide-mediates site-directed mutagenesis reactions resulted in the production of a SalI site 5' to tetK allowing a convenient means to introduce these constructs into pCBSal. In addition to the SalI site, pGG57 (SEQ ID NO:6) contains tetK with an ATG start site and pGG71 (SEQ ID NO:7) contains tetK with a TTG start site. Other than these changes both of the tetK constructs are identical at the DNA level.

Figure 3A:
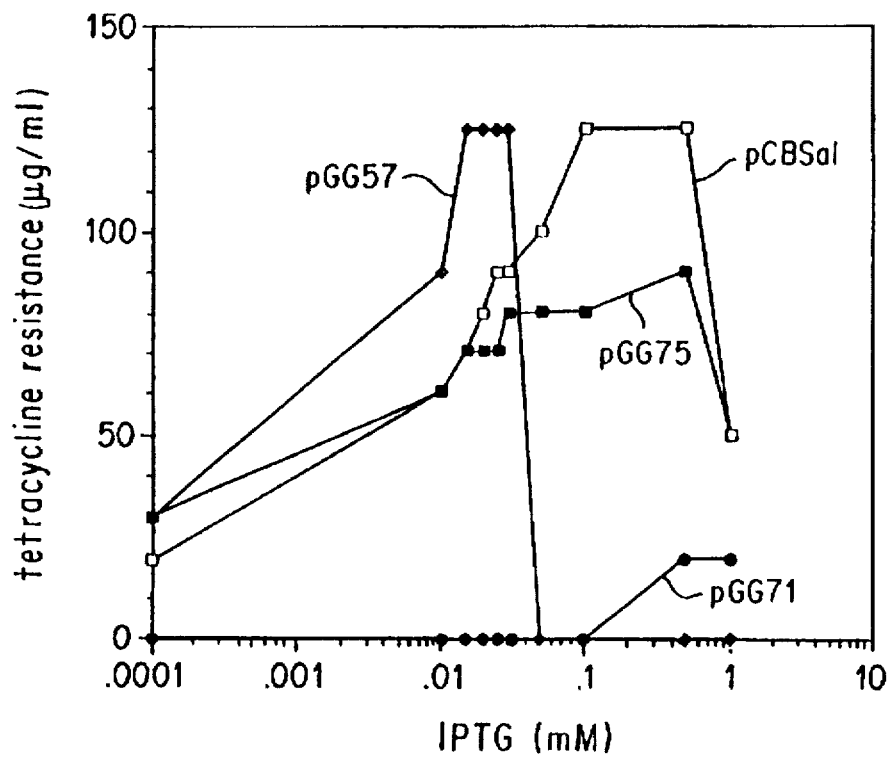

FIG. 3A. The tetracycline resistance profile conferred by the plasmids pCBSal, pGG57, pGG75 and pGG71 in *E. coli* strain MC1061. Cells are grown in Luria Broth liquid media, serially diluted with 0.85% saline, and spread onto agar plates containing increasing concentrations of tetracycline in the presence of increasing concentrations of IPTG. Plates were incubated at 37° C. for 16 hours. The concentration of tetracycline resulting in at least 90% loss of colony forming units ($LD_{90}$) is indicated.

Figure 3B:
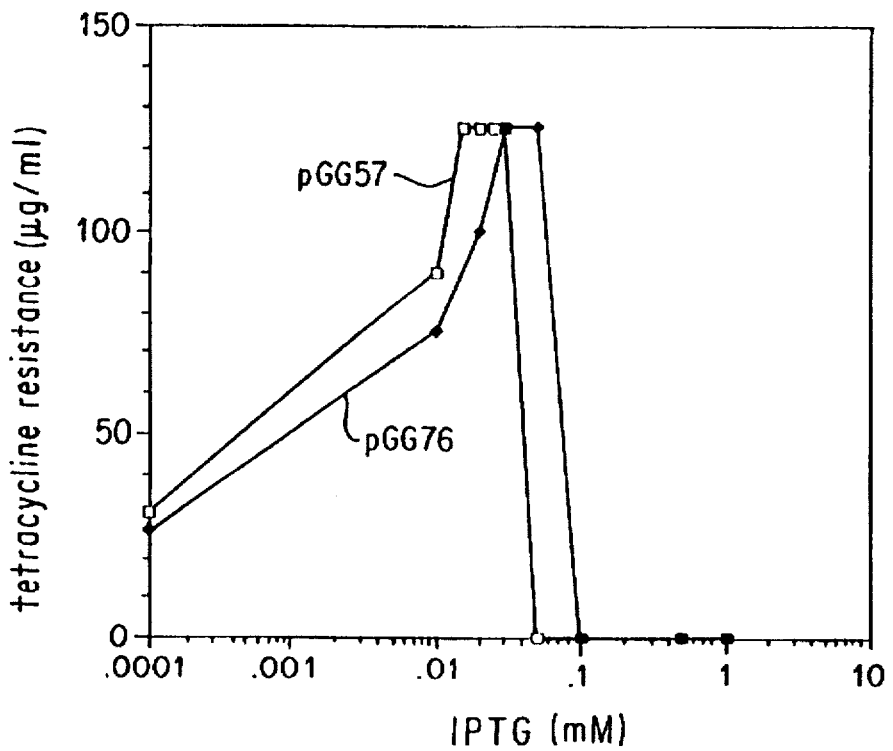

FIG. 3B. The tetracycline resistance profiles of *E. coli* MC1061 containing pGG57 or pGG76, which both contain tetK and identical regulatory elements, but differ in their plasmid replication region. The procedure used to obtain these profiles is identical to the protocol described in figure legend 3A.

FIG. 4. The plasmids listed are derivatives of pGG57. The plasmid pGG76 is a pACYC184 derivative of pGG57 containing lacI and tetK. The plasmids pGG77 and pGG84 are deleted for DNA sequence within the tetK coding region.

Figure 5:
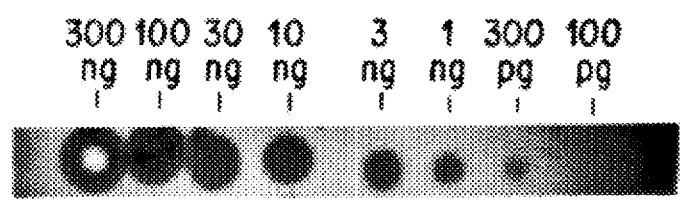

FIG. 5 illustrates the results of a plate assay to detect tetracyclines. In this experiment 10 μl spots containing the amount of tetracycline indicated is applied to the lawn of cells grown as described in the text, and after three hours incubation the chromogenic substrate is applied. The amount of tetracycline in each spot is indicated. 300 pg of tetracycline can always be detected. When higher amounts of tetracycline are applied, a zone of growth inhibition can be observed, surrounded by a ring of induction.

Figure 6:
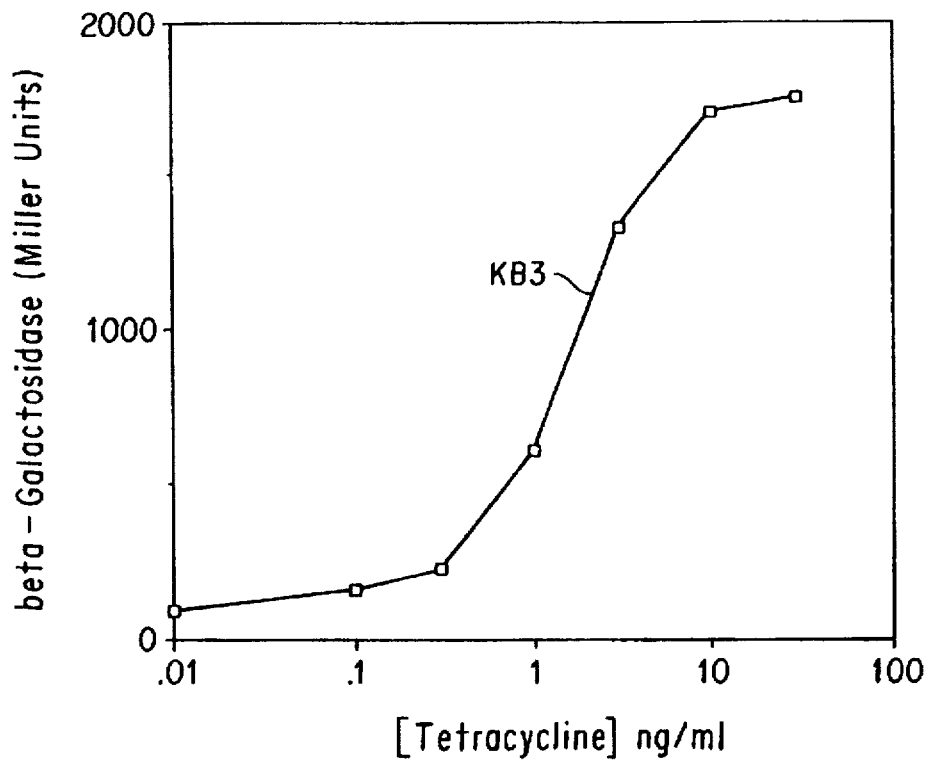

FIG. 6 illustrates a liquid assay to detect tetracyclines. Samples are added to aliquots of cells, as described in the text, and induction is numerically measured by performing β-galactosidase assays. The specific activity of β-galactosidase, in Miller units (10), is indicated when cells grow for 4 generations in the presence of tetracycline at the indicated concentration. The presence of 5–10 ng/ml of tetracycline is routinely sufficient for full induction.

Figure 7:
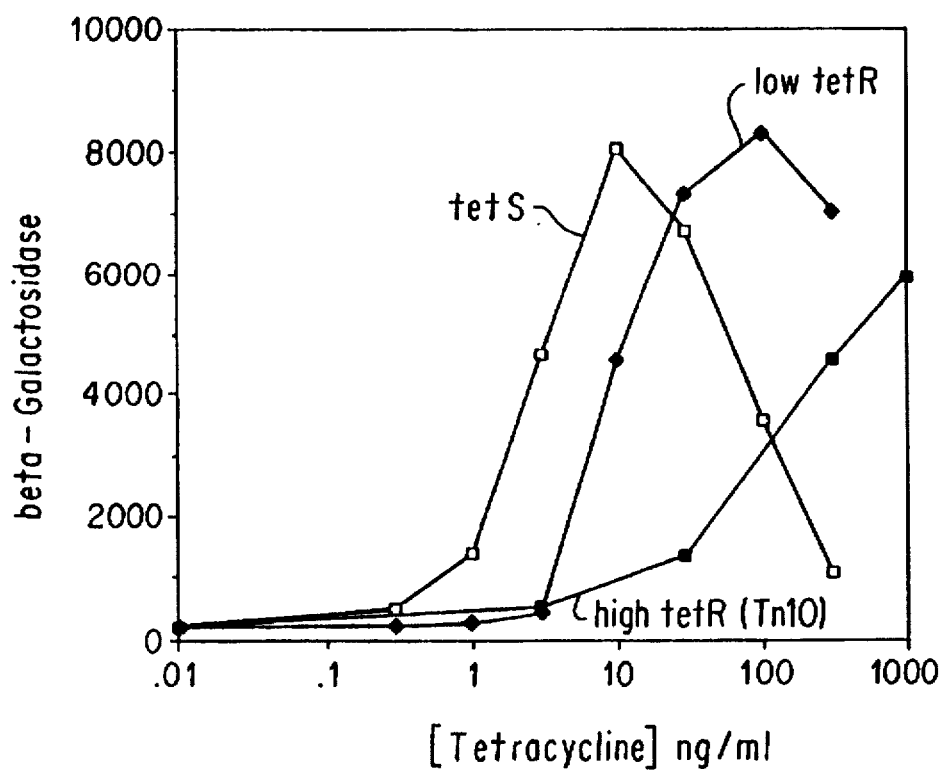

FIG. 7 shows the induction of tetracycline-sensitive and resistant strains in liquid culture. Cells are added to tetracycline to the final concentration indicated as described in FIG. 7. The sensitive strain is the tetracycline screening organism KB3ind, which induces fully when grown in the presence of 5–10 ng/ml of tetracycline. In contrast, the strain containing the Tn10 element, conferring strong tetracycline resistance, induces fully when the concentration of tetracycline is above 1 μg/ml. Strain KB4, a modestly tetracycline-resistant organism due to the low constitutive expression of the tetracycline efflux pump, exhibits a low background of induction in the presence of 5 ng/ml of tetracycline, but full induction when 30 ng/ml of tetracycline is present.

Figure 8A:
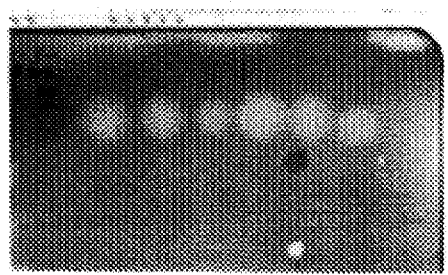
Figure 8B:
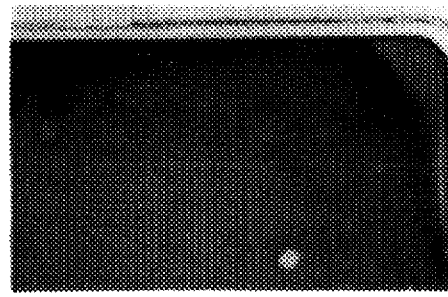
Figure 8C:
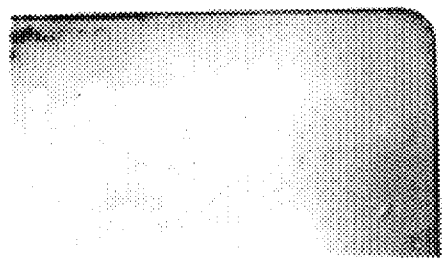

FIG. 8 (Parts A, B and C) illustrates the results of the various assays when an active agent is present in culture. Extractions from a fermentation broth are prepared by solvent extraction and C18 reverse-phase column chromatography. A ten-fold concentrate of the fermentation broth is applied to the Tetracycline Assay plate (FIG. 8A), the Inhibition Assay plate (FIG. 8B), and the Synergy plate (FIG. 8C) as described in the text. A compound antagonizing the tetracycline efflux pump is expected to cause growth inhibition of strain KB4 in the Synergy Assay (growth in the presence of 5 μg/ml of tetracycline), induction of β-galactosidase in strain KB4 in the Inhibition Assay (growth in the presence of 5 ng/ml of tetracycline), but no induction in strain KB3ind in the Tetracycline Assay. Two independent samples are prepared, and 10 μl samples of the ten-fold concentrate, three-fold concentrate, and unconcentrated sample are applied to each plate as indicated and incubated for 3 hours. Induction or growth inhibition are observed following the chromogenic overlay. The active component in the preparation causes induction only in the Inhibition Assay, and differential growth inhibition in the Synergy Assay. The active component is isolated and determined to be nocardamine, a siderophore. Other distinct siderophores also exhibit this same activity.

Figure 9:
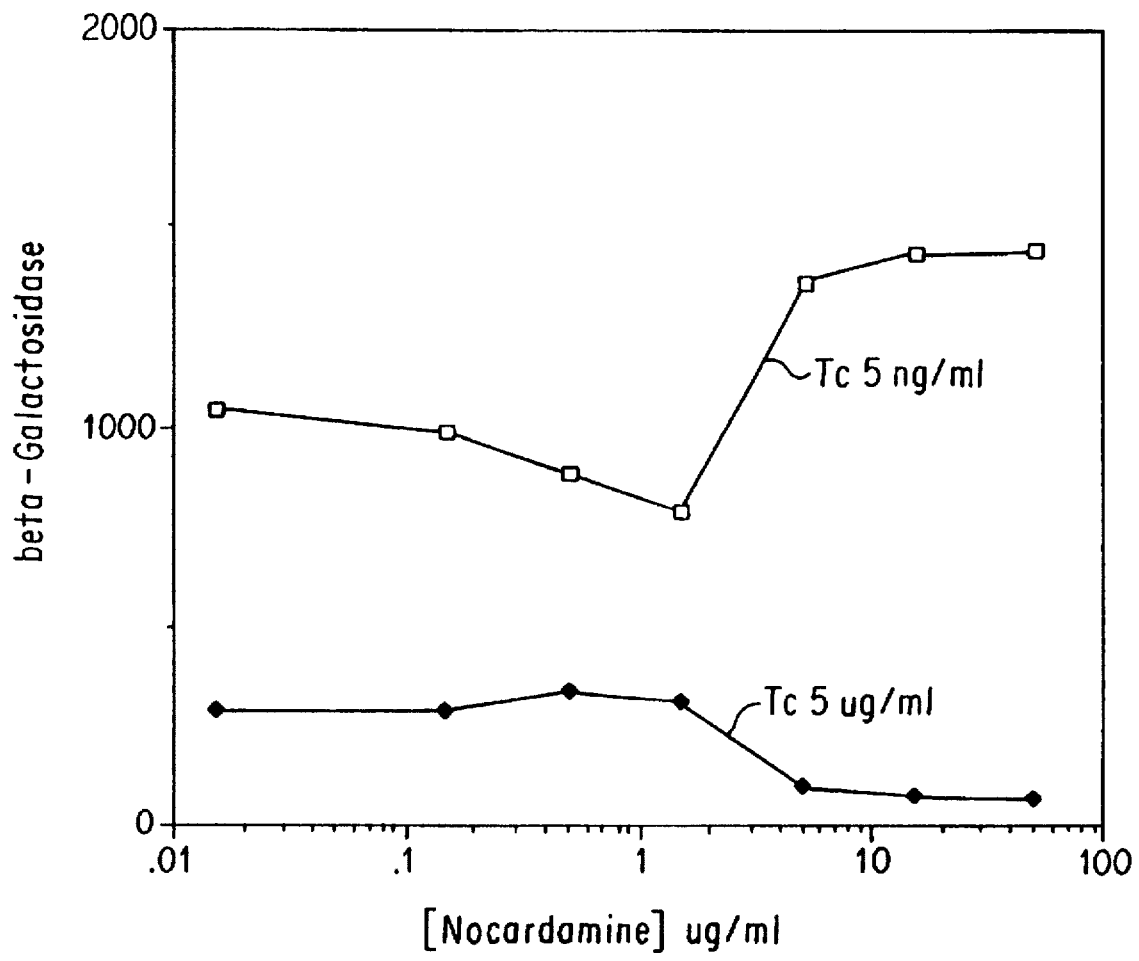

FIG. 9 illustrates the results of liquid assays for inhibitors of the tetracycline efflux pump. Inhibitory activity is assayed in liquid culture by growing strain KB4 in medium lacking tetracycline and then transferring to medium containing 5 ng/ml of tetracycline, a sub-inducing level of tetracycline due to the action of the efflux pump. Nocardamine is also added as indicated. After 4 generations of growth, the specific activity of β-galactosidase is determined in Miller Units (10). Induction of β-galactosidase can be detected when nocardamine is present above 5 μg/ml. Alternatively, aliquots of KB4 are transferred to a medium containing 5 μg/ml of tetracycline and the nocardamine concentration indicated. A marked decrease in β-galactosidase is observed, in parallel with a decrease in growth rate (not shown). Both of these responses indicate that nocardamine interferes with the efflux of tetracycline by the efflux pump.

Figure 10A:
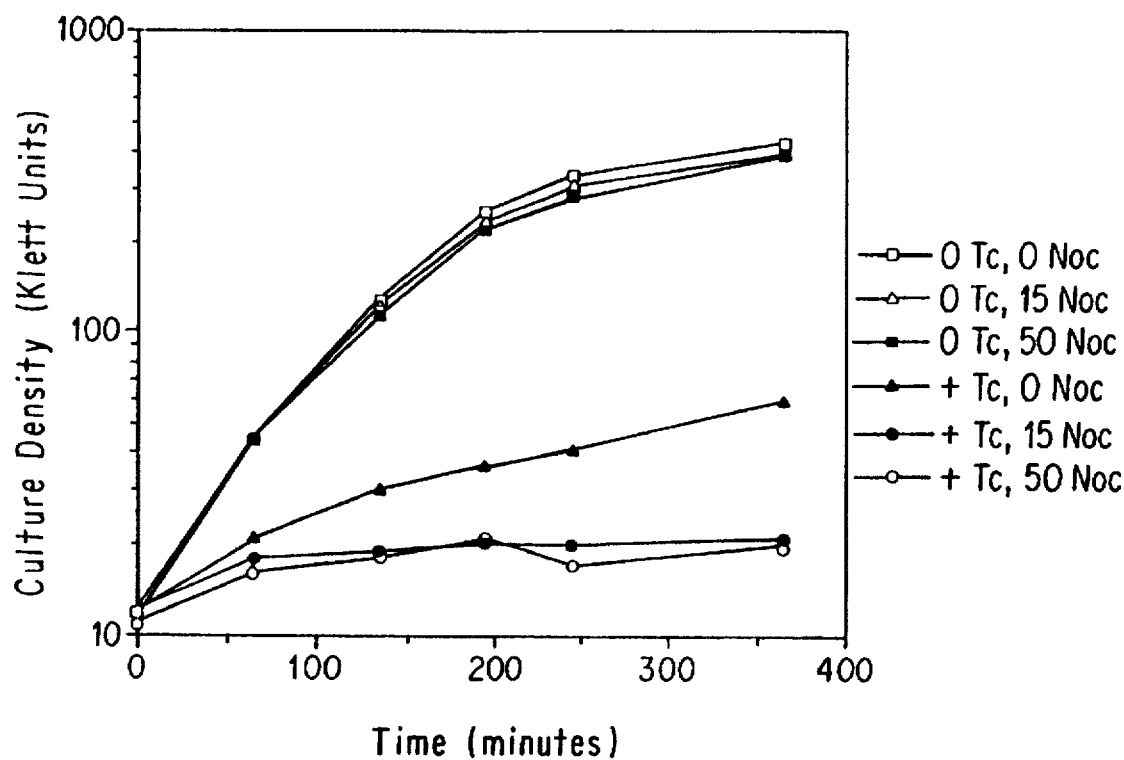
Figure 10B:
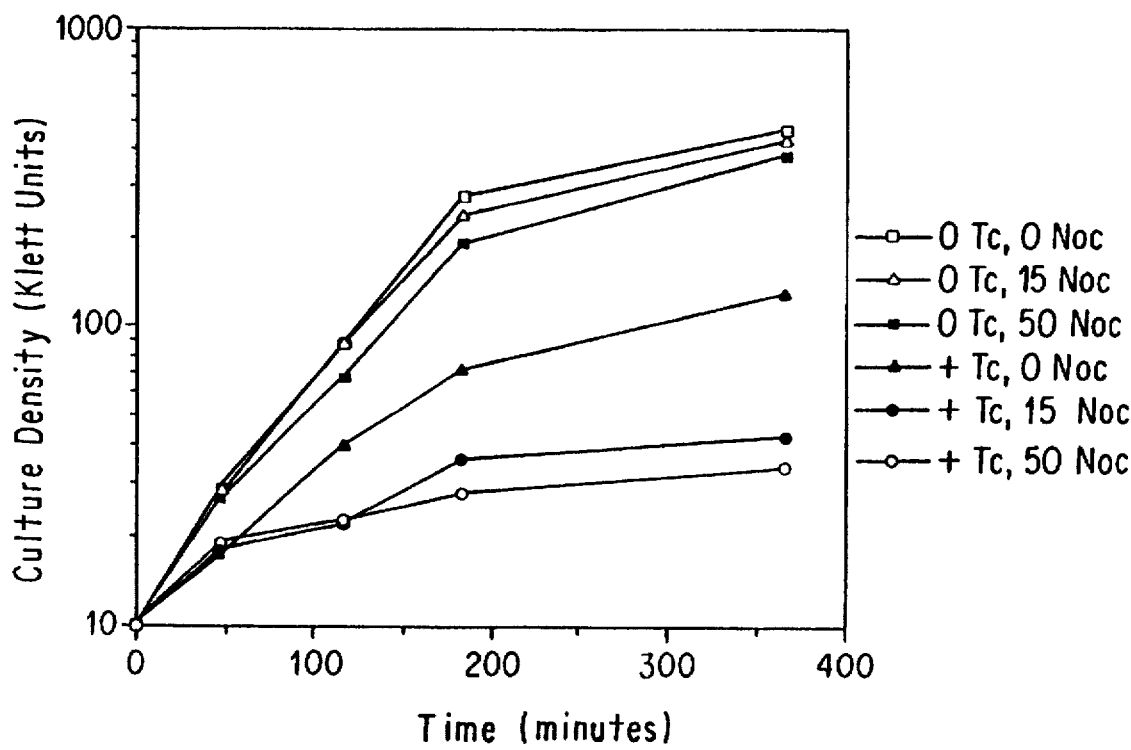
Figure 10C:
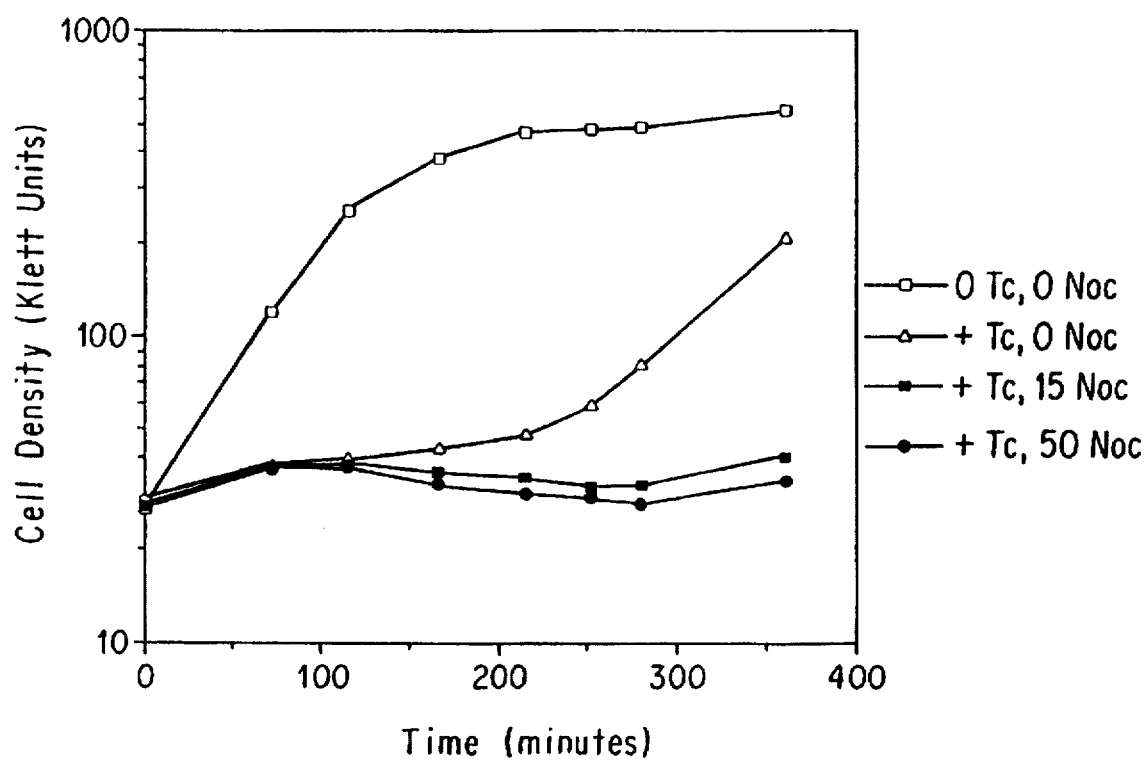

FIG. 10 (Parts A, B and C) illustrates the effect of nocardamine on the growth of tetracycline sensitive and resistant cells. Cells are grown in LB medium lacking tetracycline, as described in the text, and then aliquots are added to medium containing no tetracycline, or a sub-inhibitory concentration for the particular strain. Nocardamine (μg/ml) is present or absent as indicated. For strain KB3ind, the tetracycline-sensitive strain, the sub-inhibitory concentration of tetracycline is 0.5 μg/ml. For the Tn10 derivative of strain KB3ind, 20 µg/ml of tetracycline is the sub-inhibitory level. For strain KB4, the modestly tetracycline-resistant organism, 5 µg/ml of tetracycline is the sub-inhibitory concentration. Nocardamine has little effect when tetracycline is absent, whereas nocardamine causes severe growth inhibition in combination with tetracycline for the tetracycline resistant strains. However, nocardamine, with tetracycline, also affects the growth of the tetracycline-sensitive strain, leaving open the possibility that nocardamine could increase the uptake of tetracycline into cells.

SUMMARY OF THE INVENTION

The present invention provides microorganisms susceptible to induction by tetracycline which are further specifically adapted for use in tetracycline related assays. The microorganisms are modified so as to permit growth at 37°0C., the preferred temperature for the assay, and to not be susceptible to induction by DNA damaging agents, which can cause false positives in assays for the presence of tetracycline. In a preferred embodiment, the microorganisms are further modified so as to confer very low-level resistance to tetracycline; such microorganisms are particularly well adapted for use in assays for detection of inhibitors of tetracycline efflux pump inhibitors since they are extremely sensitive to even small quantities of a pump inhibitor. Preferably, the microorganism is E. coli.

The microorganisms provide the basis for novel assays, both for detection of compounds having tetracycline-like activity (tetracycline assays) and for the detection of pump inhibitory compounds. The assay method for detection of tetracycline-like compounds utilizes a microorganism having the following characteristics: (a) an indicator gene fused to a tetA promoter, as a single- or low-copy number gene; (b) a tetR promoter expressed at low levels; (c) is refractory to induction by DNA damaging agents. In a preferred embodiment, the microorganism is also (d) capable of growth at 37° C. The microorganism is cultured in a medium which does not contain tetracycline and is contacted with a sample to be tested for the presence of tetracycline-like compounds. The culture is also contacted with a re-agent capable of producing a detectable signal when the microorganism's indicator gene is expressed. This reagent may be present in the culture medium, or may be added subsequently, depending on the particular system used. The culture is observed for the presence or absence of a detectable signal, thereby indicating the presence or absence of tetracycline-like activity in the test sample.

Because the tetA gene of TN10 is expressed only when cells encounter tetracycline, expression from the tetA promoter is a good indicator of tetracyclines. For ease of detection and sensitivity, in a preferred embodiment, a gene fusion is used that contains the transcriptional signals (the promoter and operator sites) from tetA adjacent to the lacZ structural gene, which codes for β-galactosidase. In a particularly preferred embodiment, the following factors contribute to the sensitivity and specificity of the assay: (1) the fusion of the tetA control region to the lacZ structural gene is in single copy within bacteriophage λ, (2) the tetR gene is integrated in the opposite orientation relative to the bla gene on the plasmid, resulting in a low level of repressor, (3) the λ cIind allele permits growth at 37° C. but prevents induction by DNA damaging agents, and (4) the timing of the assay and the use of sensitive chromogenic reagent (6-bromo-2-naphthyl-β-galactopyranoside and fast blue RR) indicated by the presence of the detectable signal.

Two methods for detection of tetracycline efflux pump inhibitors are also provided. A Synergy Assay detects compounds capable of inhibiting the efflux pump in the presence of tetracycline. In this assay, the microorganism used has the following traits: (a) an indicator gene fused to a tetA promoter as a single or low copy number gene, (b) a tetR gene expressed at low levels; (c) is refractory to induction by DNA damaging agents; and (d) a tetracycline efflux pump gene which confers a low level of resistance to tetracycline; preferably the microorganism is capable of growth at 37° C. The microorganism is grown in a medium containing sub-inhibitory but inducing levels of tetracycline, and is contacted with a sample to be tested for the presence of an efflux pump inhibitor; the culture is also contacted with a reagent capable of producing a detectable signal when the indicator gene is expressed, either in the culture medium or by subsequent addition. The presence or absence of a detectable signal is observed, thereby indicating the presence or absence of a pump inhibitor. The absence of the signal in this assay indicates growth inhibition, and therefore the presence of a useful inhibitory compound in the test sample.

In an alternate assay, the Inhibition Assay, the microorganism as described above for the Synergy Assay is grown in a medium containing non-inhibitory and sub-inducing levels of tetracycline and a compound which produces a detectable signal when the indicator gene is expressed; the microorganism is contacted with the test sample, and the presence or absence of the detectable signal in the medium is observed. This assay identifies inhibitors of the tetracycline efflux pump by observing induction, i.e., the presence of the detectable signal in a medium which, prior to contact with the test sample, contained only sub-inducing levels of tetracycline.

The following terminology is used throughout the specification and claims: tetA is used to refer to the gene which confers tetracycline resistance in transposon Tn10; tetK refers to the gene encoding the tetracycline efflux pump in *Staphylococcus aureus*; and tetC refers to the gene encoding the tetracycline efflux pump from plasmid pB322.

DNA constructs and expression vectors useful in developing the present screening assays and microorganisms are disclosed in U.S. Pat. No 5,384,259, the contents of which are incorporated herein by reference.

DETAILED DESCRIPTION OF THE INVENTION

The claimed DNA sequences are originally obtained by modification of the BamHI-NcoI fragment found within the plasmid pCB258 gene that encodes the tetracycline pump from transposon Tn10 responsible for tetracycline resistance (the tetA gene). An inducible expression system for tetA regulation has been disclosed by Eckert and Beck (7), as described above. This system, however, may be unacceptable for expression of tetracycline pump genes because it potentially expresses the pump too strongly. Additionally, it lacks a convenient restriction site for cloning of genes other than tetA, and contains a repressor binding site that is incompatible with its use in microorganisms to be used to detect tetracycline pump inhibitors. Therefore, the plasmid, in particular the BamHI-NcoI fragment containing the coding region and a portion of the regulatory region of the tetA gene is investigated in an attempt to provide a sequence which would permit cloning of other genes into the plasmid, as well as permitting low level expression of the genes so cloned.

A schematic diagram of the tetA gene, including a portion of the regulatory region, of transposon Tn10 is provided in FIG. 1. Tetracycline resistance in enteric bacteria generally is mediated by the transposon Tn10, through the action of two genes. Briefly, the expression of pump gene tetA is regulated by the tetR gene product, a repressor; two tetR repressor binding sites are located slightly upstream of the tetA coding region. The plasmid pCB258 of Eckert and Beck was engineered to achieve controlled expression of the tetA gene by cloning the Tn10 tetA gene behind a tac promoter; expression in this system is under control of the lac repressor encoded on the same plasmid. There was no indication by Eckert and Beck to what extent, if any, either of the tetR repressor binding sites are present on the recombinant plasmid, although restriction analysis indicates that one binding site nearest the tetA coding region remains.

Figure 1B:
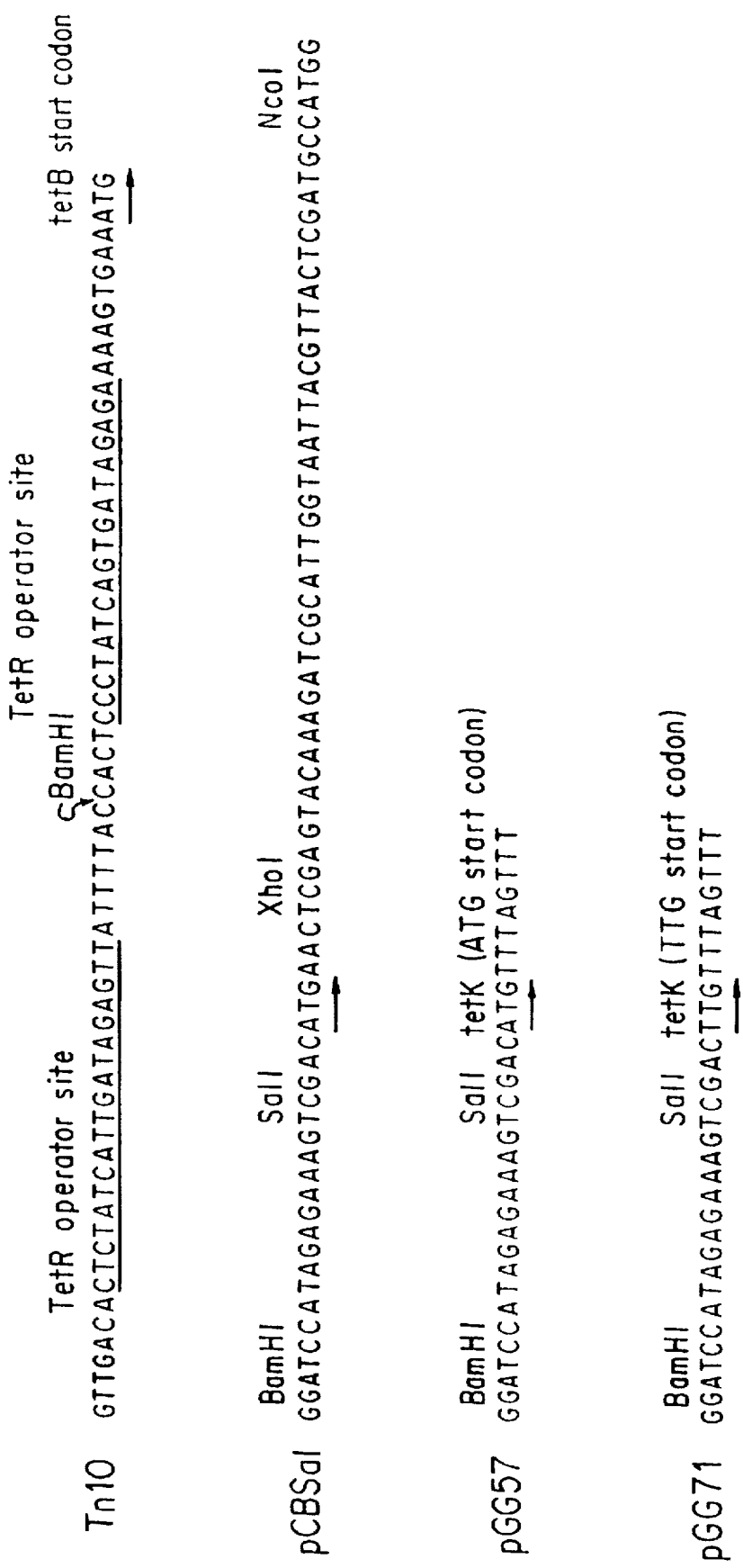

In an attempt to achieve expression of S. aureus tetK, the pCB258 plasmid provides a convenient starting point; in particular, attention is focused on the region between the BamHI and NcoI sites of the vector. The details of the sequence of this region are found in FIG. 1B. Inspection shows that there is not a convenient restriction site into which the tetK gene can be cloned. To overcome this problem, a pair of oligomers are synthesized that can hybridize to form a DNA fragment with the desired modifications, and containing a BamHI and NcoI sticky end for cloning into the BamHI and NcoI sites of the vector. One strand is illustrated in FIG. 1B (labelled "pCBSal"). The substitution of this fragment in the vector results in the introduction of two unique restriction sites, a SalI site upstream and adjacent to the initiation codon, and an XhoI site within the coding region, which does not alter the amino acid sequence of the tetA protein. The changes including the SalI site have an unexpected effect. When this vector is used to express tetA in E. coli, a higher concentration of IPTG is required to induce the expression of the tetA gene than is required by the parental vector. This suggests that the change alters the strength of the tetA ribosome binding site ["ribosome binding site" being interpreted in the broad sense as defined by Gold and Stormo (22)], rendering it less efficient.

This construct is then used to attempt expression of the S. aureus tetK gene in E. coli. Since the unmodified tetK gene, when present in E. coli, does not confer resistance, some alteration is required. To achieve E. coli expression, the tetK gene, in bacteriophage M13, is modified to contain a SalI site immediately 5' to the start site for cloning purposes. Additionally, to facilitate expression in E. coli, the normal tetK TTG start site is mutagenized to ATG. The tetK gene thus modified is then ligated into the pCBSal vector.

The plasmid construct is used to transform E. coli for tetK expression. The effect of the apparently weakened ribosome binding site in the expression system, balanced by the presence of an E. coli ATG start site, results in a strain that confers resistance to just 25 µg/ml of tetracycline in the absence of inducer, and therefore produces a low level of the S. aureus tetK gene product.

Although strains with plasmids containing the pCBSal type construct express low levels of the gene, it is possible to decrease the level of expression even further by removing the strong tac promoter preceding the tet gene. In both the parental pCB258 and Plasmid pCBSal, expression is regulated by this promoter. However, substantial expression occurs from pCB258, and to a lesser extent from pCBSal, even in the absence of inducer. Expression can be reduced further by cloning the gene of interest and its ribosome binding site (i.e., the SD and ATG), but not its transcriptional start signals, into another plasmid. The position in the new plasmid is preferably not within a gene that is actively transcribed. The insert containing the gene and its ribosome binding site can be cloned in either orientation at a particular location in a plasmid by known methods, e.g., if the vector and insert are cut by the same enzyme.

In the context of developing a screening microorganism to detect tetracycline pump inhibitors, this type of strain is ideal. Other organisms, containing a tetracycline efflux pump, for example, a strain carrying transposon Tn10, have a number of disadvantages as a screening organism. Tn10 confers a high level of resistance to tetracycline, and thus, there are relatively many pumps to inhibit before a signal might be detected in a fully tetracycline resistant strain. Also, the tetA gene of Tn10 is regulated; inhibition of efflux pumps will result in an increased synthesis of new efflux pumps, as a response to the increased intracellular level of tetracycline, so that the effect of an inhibitor will be minimized by a fully tetracycline resistant strain. Transposon Tn10 also contributes the repressor gene tetR, as well as the tetA gene; increased expression of the repressor may cause diminished sensitivity (9). Even pCB258, the Eckert and Beck plasmid, which has been modified in such a way that expression can be controlled to some extent, still has its disadvantages. A low, constitutive level of tetA expression is optimal for a screening organism to detect inhibitors of the tetracycline efflux pump, a task to which the Eckert and Beck system is not ideally suited, for several reasons. First, the level of tetA expression in strains containing pCB258 is still too high (confers resistance to 40 µg/ml; MIC=50 µg/ml, in the absence of IPTG) for optimal use in screening for pump inhibitors. Second,lactose, which would induce expression of tetA on plasmid pCB258, might be present within fermentation broths to be screened, interfering with the screen. Further, restriction analysis of plasmid pCB258 indicates that one of the two operator binding sites of the tet regulatory region is present in plasmid pCB258. In a screening organism utilizing the tet regulatory elements and therefore containing the tetR gene, a low, constitutive level of tetA expression could not be achieved. Finally, there is no convenient restriction site in the appropriate region to permit insertion of an alternate gene, such as tetK.

It will be apparent that certain modifications within the specific pCBSal sequence can be made without altering the overall effect on the useful characteristics of the sequence. For example, it is contemplated that the SalI site may be replaced with other useful restriction sites. It will also be understood that, depending on the gene to be expressed, and the desired level of expression, alternate promoters can be used as well, e.g. E. coli trp, λ PL, ara. Also, as will be shown in the following examples, the invention is not limited to use of a particular plasmid, as expression can be readily achieved on unrelated plasmids, and the modifications which may be required to insert the desired sequence into other plasmids, i.e., modification of restriction sites, are within the skill of the art given the disclosure of the present specification.

The foregoing vectors provide a basis for development of assays to detect pump inhibitors. However, additional manipulations are required to create a microorganism optimally adapted for use in an assay system. Certain traits are desirable for purposes of developing an assay microorganism useful in either a Tetracycline Assay or in a Pump Inhibitor Assay, and no previously available microorganism contains all the required traits. Thus, an ideal base microorganism is needed before the assay system can be implemented.

For purposes of developing the present assays, the previously described strain containing λRSTET 158-43 provides a convenient base from which to develop an ideal assay organism (9). λRSTET 158-43 has certain basic traits which are useful in designing any assay organism. For example, λRSTET 158-43 has a convenient indicator system which allows visual detection of the presence or absence of the occurrence of the anticipated biological event, in this case, the lacZ gene, which encodes the enzyme β-galactosidase, is fused to the tetA promoter, from transposon Tn10, in the absence of the tetA gene. As was described above, transcription from the tetA promoter is regulated by the tetR gene product, the tetracycline repressor. When cells are grown in the absence of tetracycline, then transcription is not initiated from the tetA promoter. When cells encounter tetracycline, the tetracycline enters the cell, binds and inactivates the repressor, and mRNA is made; in other words, in the presence of tetracycline, the tetA promoter is induced and expression of the tetA gene occurs. Similarly, in the case of a tetA-lacZ fusion, induction and expression of β-galactosidase is measured. This type of detection system is particularly useful, because of the ease of recognition of the color-change indication on the assay plate when the β-galactosidase substrate is included in the medium. However, it will be recognized that the assay system is not limited to the use of a lacZ fusion; any other indicator system which provides a detectable signal upon induction of the tetA promoter is acceptable, such as the luciferase system or the chloranphenicol acetyl transferase system.

In a preferred embodiment, the fusion construct is present in the assay microorganisms as a single gene copy. If the fusion gene were to be cloned on a multi-copy plasmid, the background of the indicator (e.g., β-galactosidase) produced when cells are grown without tetracycline in the medium would be considerably higher, as in the described organism (11). In the following examples, an embodiment is described in which the lacZ-tetA fusion is located on a λ bacteriophage integrated into the chromosome of E. coli; however, insertion on a single- or low-copy number plasmid is also acceptable.

A further modification, specifically with respect to the tetR gene, also contributes to the sensitivity of the assay. Although tetR is normally present on a multicopy plasmid, in a preferred embodiment, it is present at low levels. By "low level" of repressor is meant an amount which will confer sensitivity to 10 ng or less of tetracycline. One way in which this is achieved is by cloning the tetR gene without its own promoter, inserted into a plasmid gene, bla, in the "wrong" orientation (9). In this manner, very little repressor protein is made, so that the system is triggered to induce at the extremely low levels of tetracycline. An assay organism having these traits is more sensitive in detecting tetracyclines than the assay organism previously described (11).

There is a disadvantage in the organism described above (9), however, in that it cannot grow at 37° C. This is because the CI protein, the λ repressor, is temperature-sensitive and is induced in response to heating at 37° C. A variant strain of bacteria is capable of growth at 37° C., because it contains the wild-type λ repressor (19). This kind of strain has the advantage that assays can be conducted with cells that grow more rapidly at 37° C., assuring, for example, that the assay can be conducted in its entirety in a single day. It also has the advantage that inadvertent temperature variations will not affect the assay results. However, this strain, with the wild-type CI allele, has the disadvantage that it is susceptible to DNA damaging agents, such as mitomycin C in addition to tetracyclines. This class of compounds (which are very likely to be present in materials to be tested, such as fermentation broths) will also induce β-galactosidase production in this organism modified to permit growth at 37° C. This potentially creates a lack of specificity in the assay which is unacceptable. This problem is overcome by substitution of a mutated allele of the CI gene that causes the Ind-phenotype (13), resulting in a failure of λ to be induced by the SOS system. After the introduction of the ind mutation, the microorganism is suitably specific for tetracyclines.

The organism described above is useful in a variety of assays for detection of tetracyclines. For example, in a plate assay, the cells so constructed are mixed with soft agar and poured into a plate. Sample compounds to be tested are applied directly to the agar or in an impregnated disc, and incubated. After incubation, the plates are overlaid with the appropriate substrate to detect the expression of the indicator gene. For example, when using the lacZ gene, the plates are overlaid with 6-bromo-2-naphthyl-β-D-galactopyranoside and an appropriate dye; the presence of β-galactosidase is indicated by a purple spot as described (11). A liquid assay in which β-galactosidase activity is measured can also be employed (10, 12).

For use in a tetracycline efflux pump inhibitor assay, further modifications of such organisms are performed. The basic microorganism as described above is employed, with the addition of plasmids carrying efflux pump genes. To produce the most sensitive assay system, the plasmid utilized is one such as is disclosed above, which has been designed to confer a very low level of resistance to tetracycline. In a preferred embodiment, this low level of resistance is achieved by cloning the efflux pump gene and its ribosome binding site signals, but not its transcriptional start signals (promoter) into a "nonactive" region of a plasmid. As shown above, specific novel DNA constructs provide reduced expression of the genes under their control; this additional step takes an already low level of expression one step further, by removing the influence of the native promoter. Although these constructs can be employed with any tetracycline efflux pump gene, for the present assay, tetA and tetK are the preferred pumps to be tested.

In a preferred embodiment, the level of resistance conferred by the engineered plasmids is no more than 25 μg/ml of tetracycline, preferably no more than 10 μg/ml. Screens can then be conducted. In the following examples, two specific types of screening organisms are described which meet these requirements. One strain, KB4, contains the tetA gene inserted into plasmid pBT401, which confers resistance to less than 10 μg/ml, as opposed to a TN10 derivative of KB3ind, which is resistant to more than 100 μg/ml of tetracycline. The effect of the insertion of the efflux pump genes is shown in FIG. 7. Strain KB3ind is tetracycline-sensitive, and induces maximally when exposed to just 5–10 ng/ml of tetracycline. In contrast, the presence of transposon Tn10 prevents full induction until the tetracycline concentration approaches 1 μg/ml of tetracycline. The efflux pump constitutively produced in strain KB4, which results in modest resistance to tetracycline, prevents induction of β-galactosidase in the presence of 5 ng/ml more effectively than the Tn10 strain. Thus more pumps may be synthesized when strain KB4 is exposed to very low concentrations of tetracycline, resulting in a reduction in the internal tetracycline concentration of tetracycline even when compared to the Tn10 strain. However, when concentration is increased only slightly, KB4 cannot respond by making more efflux pumps, and full induction occurs when concentration of tetracycline is increased to 30 ng/ml. Thus, strain KB4 may be optimum in terms of tetracycline resistance. The strain KB5 is isogenic to KB4, except that the tetK gene is present in place of the tetA gene. The MIC of KB5 is also about 10

μg/ml of tetracycline. The tetK gene results in a similar shift in the induction curve compared with strain KB4.

Two types of assays for pump inhibitors are designed using this type of screening organism. The first is a Synergy Assay, which determines the ability of a compound or composition to kill the organism in combination with tetracycline. Preferably, the screen identifies compounds that cause growth inhibition in the presence of 5 μg/ml of tetracycline, but not in its absence. In brief, in a Synergy Assay, the screening cells are treated as described above for the tetracycline assay, except that the agar medium contains 5 μg/ml of tetracycline which is near the MIC for the strains to be used in the screen. Growth inhibition is detected by the lack of purple color. Alternatively, cells are treated as described above for the tetracycline liquid assay, except that cells are shifted to a medium containing 5 μg/ml of tetracycline.

The second type of assay is an Inhibition Assay. This assay relies on the fact that full induction of β-galactosidase occurs in the presence of 5–10 ng/ml of tetracycline in strain KB3ind (FIG. 7), the sensitive strain. However, the intracellular concentration of tetracycline tends to be reduced in resistant strains due to the action of the efflux pump. It therefore may be that more tetracycline in the medium would be required to accumulate sufficient tetracycline inside the cell to induce. This assay is designed to detect compounds that cause β-galactosidase (or other indicator gene) induction in the presence of sub-inducing levels of tetracycline for a resistant strain. A particularly promising compound would be one which causes growth inhibition in the synergy assay, and induction in the inhibition assay.

The following non-limiting examples further illustrate the practice of the present invention.

EXAMPLES

Construction of Plasmid pCBSal

A pair of synthesized complementary oligomers shown below as SEQ ID NOS: 8 and 9, respectively, containing BamHI and NcoI ends, is ligated into the large BamHI/NcoI fragment of pCB258 (7), using the standard ligation conditions (8).

GATCCATAGAGAAAGTCGACATGAACTC-GAGTACAAAGATCGCATTGGTAAT-TACGTTACTCGATGC (SEQ ID NO:8)
GTATCTCTTTCAGCTGTACTTGAGCT-CATGTTTCTAGCGTAACCATTAATG-CAATGAGCTACGGTAC (SEQ ID NO:9)

Plasmid pCBSal is partially deleted for a tetracycline operator binding site found in pCB258, and contains two unique restriction sites: a SalI site immediately 5' to the start codon tetA and an XhoI restriction site in the coding region of tetA which does not alter the amino acid sequence encoded by the gene. The BamHI site is also unique in pCBSal.

Construction of Expression Vectors Containing tetK

A pCBSal derivative that expresses the tetK gene in *E. coli* is constructed in two steps. First, the tetK gene in the M13 bacteriophage, MC71 (3), is mutagenized using oligonucleotide-mediated site-directed mutagenesis according to Kunkel, et al. (15). The oligomer 5'-CCTCAAGTAAAGAGGTCGACATGTTAGTTTAG-3' (SEQ ID NO:10) is used to alter the naturally occurring tetK start codon to ATG, and to introduce a SalI restriction site just upstream of the new start codon. Then the RFI phage DNA containing the modified tetK gene is digested with SalI/HindIII and ligated into the large fragment generated when pCBSal is digested with SalI/HindIII, resulting in plasmid pGG57. An isogenic plasmid containing the original TTG start codon, called pGG71, is also constructed in two steps. The oligomer 5' AAGAGGTCGACTTGTTTAGT-TAAG 3' (SEQ ID NO:11) is used to introduce a SalI restriction site adjacent to the natural (TTG) translational start site for tetK. Plasmid pGG71 is constructed in the manner outlined above. The sequences of all phage constructs are verified using DNA sequence analysis according to standard procedures (8).

The tetK gene is cloned onto an alternative expression vector by digesting plasmid pGG57 with ScaI and HindIII enzymes, and ligating the 2.7 Kb fragment to the large fragment generated by digesting plasmid pACYC184 with HincII and HindIII enzymes using standard techniques (8). The resulting recombinant, designated pGG76, contains the lacI gene, the tac promoter, followed by the tetK gene containing the ATG initiation codon.

The tetC gene encoding the tetracycline efflux pump from plasmid pBR322 is transferred into this expression system by using polymerase chain reaction to engineer a SalI site just prior to the ATG start codon, using standard techniques (8). The resulting plasmid is digested with SalI and NheI enzymes, and the small fragment containing the 5' end of the tetC coding region is isolated. The 3' end of the tetC is isolated by digesting with AvaI enzyme, filling in with Klenow enzyme, and digesting with NheI enzyme. The entire tetC coding region is ligated into the expression system by means of a three-way ligation, in which the expression vector is prepared by digesting with HindIII, filing in, and digesting with SalI enzyme. (A two-way ligation is not straightforward due to the presence of a SalI site within the tetC gene.) The plasmid containing the entire tetC gene is isolated following transformation of strain MC1061, selecting for ampicillin resistance. Standard techniques are used (9).

Tetracycline resistance of plasmid pGG58 within strain MC1061 is 15 μg/ml, even when high levels of IPTG are added to the medium. The level of tetracycline resistance is at least five times lower than tetracycline resistance conferred by plasmid pBR322, indicating that the optimal level of expression is not attained. Therefore mutants are selected that can survive the presence of 100 μg/ml of tetracycline in LB agar that also contained 0.1 mM IPTG, to permit some induction. One mutant derivative, containing plasmid pGG75, is isolated that is used in subsequent studies. The mutation is determined to be located on the plasmid, since transformants breed true for high tetracycline resistance. The possibility of a mutation within the tetC coding region is eliminated by sequencing the entire tetC coding region, and finding only wild type sequence, using standard techniques (8).

Determination of tetracycline resistance

*E. coli* strain MC1061 containing plasmid pCBSal, pGG57, pGG71, pGG75 or pGG76, is tested for tetracycline resistance by growing overnight cultures in Luria Broth (2) containing 50 μg/ml of ampicillin. A 1:50 dilution of each overnight culture is inoculated into fresh L-A broth. Exponentially growing cells are serially diluted in 0.85% saline such that each plate is inoculated with 200–500 cells. The cells are spread on L-agar (pH 6.8–7.0) containing ampicillin (50 μg/ml), containing a range of IPTG and tetracycline concentrations (0.001 mM–1.0 mM IPTG and 0–200 μg/ml of tetracycline). The plates are incubated at 37° C. for 18–20 hours and the minimum inhibitory concentration (MIC) is determined as the concentration of tetracycline preventing at least 90% of the cells from forming colonies (LD 90). A comparison of pCBSal, pGG57, pGG75 and pGG71 is shown in FIG. 3A. Plasmid pCBSal confers the same level of tetracycline resistance when compared with pCB258; however, pCB258 confers higher resistance in the absence of IPTG (MIC=50). Furthermore, just 0.1 mM IPTG is sufficient to kill cells containing pCB258, whereas 1 mM of IPTG is necessary to kill cells containing pCBSal. Thus, an alteration to the ribosome binding site of pCBSal is indicated. Plasmid pGG57, containing the tetK gene with an ATG start codon, also confers resistance when grown at low levels of IPTG, and like expression of tetA, further induction causes cell death. Plasmid pGG71 containing a TTG start codon, confers extremely low levels of resistance, which occurs only at high IPTG levels. This result indicates the importance of the ATG start site in expression of the tetK gene in E. coli.

The results of pGG76 tetk expression are shown in FIG. 3B. Plasmid pGG76 contains the origin of replication of pACYC184, whereas plasmid pGG57 relies on pBR322 origin. As the figure shows, upon induction with IPTG, E. coli MC1061 carrying pGG76 shows a similar tetracycline resistance profile to MC1061 carrying pGG57, except that more IPTG is required to achieve maximum tetracycline resistance. This is consistent with the fact that pACYC184 derivatives are present in lower copy number than pGG57, and therefore might be expected to require more IPTG to confer full resistance. Overall, these results show that the regulatable expression of tetK can be used in unrelated plasmid types.

Construction of an Unregulated tetK Expression Plasmid

The plasmids pGG56, pGG71, pGG76, and pCBSal all are useful in lower level expression of the tet genes in that the feature of regulation by the tetR gene product is removed, and the ribosome binding site is altered so as to weaken translation. However, the plasmids all contain a regulatory element, the lacI gene, which regulates the inducible tac promoter. For purposes of the screening microorganism, it may be desirable to eliminate this final level of regulation, so that the tetK gene is expressed at a low constitutive level. To this end, a derivative of plasmid pBT401 (9) containing the tetA gene of transposon Tn10 is constructed by digesting plasmid pCBSal with SmaI restriction enzyme and ligating the small fragment into plasmid pBT401 that is digested with BamHI enzyme and filled in with Klenow enzyme as described. In the construct that confers tetracycline resistance, the gene is in the same orientation as the aph gene (kanamycin resistance), determined by restriction analysis. When the gene is in the opposite orientation, no tetracycline resistance is detected. An isogenic plasmid containing the tetK gene of S. aureus is similarly constructed using plasmid pGG57 as the source of tetK.

These plasmids are used to transform an appropriate E. coli strain for use in screening assays for tetracycline efflux pump inhibitors.

Substrate Specificity of Tetracycline Efflux Pumps

Previous studies suggest that tetracycline efflux pumps vary in their ability to recognize and pump out different tetracyclines (11). This interpretation is limited by alternative explanation. It is possible, for instance, that differences can be attributed to susceptibility of the host strain. Furthermore, if one efflux pump confers stronger resistance to tetracycline, it is difficult to distinguish whether low-level resistance to a derivative, such as minocycline, is attributable to the ability of the pump to recognize minocycline, as opposed to its enhanced ability to pump all tetracycline substrates. It is even possible that the "better" pump is simply less lethal, and tolerated in greater numbers, rather than a more efficient pump. In order to rule out other possibilities and to look at different substrates as the only variable, the abilities of tetA-, tetC- and tetK-encoded pumps to confer resistance to a single host strain MC1061 to a variety of tetracyclines are studied using the present low-level regulated system (Table 1). Using this expression system, it is shown that the closely related efflux systems, tetA and tetC, do not show marked differences in substrate specificities to different tetracycline analogs. Furthermore, when the IPTG concentration is reduced for MC1061 carrying tetB, so that the tetracycline resistance is the same as the tetC strain, then the minor differences in resistance to other tetracyclines disappeared. In contrast the tetK efflux system does show differences in its ability to pump out tetracycline derivatives minocycline, doxytetracycline, and 6-demethyl-6-deoxytetracycline (Table 1). Thus the low-level, regulated expression system allows the ruling out of alternative explanations, and to determine true differences in substrate specificity among tetracycline efflux pumps.

TABLE 1

MIC (LD 90) of Maximally Induced tetA, tetK and tetC

|  | pCBSal | pGG57 | pGG75 |
|---|---|---|---|
| Tetracycline | 150 | 125 | 100 |
| Minocycline | 14 | 4 | 8 |
| AnhydroTc | 3 | 2 | 2 |
| oxyTc | >300 | 250 | 300 |
| DoxyTc | 40 | 7 | 20 |
| ChlorTc | 50 | 40 | 40 |
| 6-demethyl 6-deoxyTc | 20 | 7 | 20 |

E. coli MC1061 containing either pGG57, pCBSal or pGG75 were used to determine the MIC (LD 90) for tetracycline as well as six tetracycline analogs. Each plasmid required a different level of IPTG for maximum induction. MIC studies were performed in the presence of 0.01 mM IPTG for E. coli MC1061 containing pGG57. An IPTG level of 0.5 mM was required for optimum induction of E. coli MC1061 containing pGG75. E. coli MC1061 containing pCBSal required an IPTG level of 0.1 mM IPTG for maximum induction. All of these MIC studies were done in duplicate.

TETRACYCLINE ASSAY

Construction of a tet-Sensitive Screening Organism

λ Stet158-43 (9) contains (a) a transcriptional fusion of lacZ to the tetA promoter from Tn10; (b) a deletion from the bet gene to the CIII gene, the loss of the gam gene, resulting in a loss of plaque-forming ability in a RecA (recombination deficient) E. coli host strain; and (c) the cI857 allele, which causes induction and cell lysis when a lysogen is grown at 37° C. The latter trait is considered undesirable for use in the screening microorganisms. Therefore, λ crosses are conducted so as to obtain a hybrid phage retaining the desirable fusion gene, but capable of growth at 37° C. and replication in a RecA host, as well as carrying the CIind mutation which prevents induction due to DNA damaging agents. To achieve the appropriate hybrid, λ stet 158-43 is crossed with λW3 (16), which contains no fusion, but does have the CIind allele and the gam⁺ gene, allowing replication in a RecA host strain. An equal multiplicity of the two phages is used to coinfect the neutral (Rec⁺) host strain NK5031, using standard phage genetic techniques (17). The resulting phage preparation is used to infect the RecA56 derivative of MC4100 at 37° C., which allows plaque formation only to gam⁺ phage. The presence of the CIind allele is assessed by screening for turbid plaques at 37° C., because the CI857 allele encodes a temperature sensitive repressor, resulting in clear plaques at 37° C. because lysogens cannot form. The presence of the lacZ fusion is indicated by screening for blue plaques when X-gal, the indicator of β-galactosidase, is included in the medium.

After plaque purification, a phage preparation is made. A lysogen containing the blue gam⁺ phage is obtained by spotting phage onto a lawn of NK5031 cells, and streaking several times for blue colonies that can grow at 37° C.

The plasmid pBT401, containing the tetR gene, is transformed into the strain containing the hybrid λ phage by selecting for kanamycin resistance using standard procedures (8). The transformant, strain KB3ind, responds to tetracycline by induction of β-galactosidase.

Use of KB3ind in Testing for Tetracycline

To detect tetracyclines, a plate assay is developed that is similar to one described previously (11). Cells are grown in Luria Broth (adjusted with NaOH to pH 7.5) with 25 µg/ml of kanamycin to a cell density of 0.5 absorbance units (600 nm). A 25 ml sample of the culture is harvested by centrifugation and resuspended in 1 ml of broth. The cells are mixed with 25 ml of soft agar (1%, wt/vol) and poured onto 100 ml of LB (pH 7.5)+ kanamycin, within a 22 cm² NUNC plate (Corning). Samples are applied by spotting from 2 to 15 µl, or by applying a disc impregnated with a compound, and the plate is incubated for 3–4 hours at 37° C. The plates are overlaid with a solution containing 13.5 mg of 6-bromo-2-naphthyl-β-D-galactopyranoside side and 86.5 mg of fast blue RR (Sigma) dissolved in 2 ml of dimethylsulfoxide, to which 25 ml of soft agar is added. β-Galactosidase is detected by the presence of a purple spot.

To be sure that the cIind allele is functioning as expected, strain KB3ind is tested using the plate assay described above. Three µl samples containing up to 22.5 ng of bleomycin, 150 ng of mitomycin C, or 150 ng of the gyrase inhibitor cinodine (18) are spotted onto the plate, as described above. No β-galactosidase is detected, but only a zone of growth inhibitor, for the strain believed to contain the λ lysogen with the CIind allele. A control strain, NK5031 (λStet158-50) (19), which contains the cI wild type allele, responds to the three reagents by inducing β-galactosidase.

The sensitivity of the assay using the KB3ind is then determined. Using the plate assay, 10 µl of samples, containing tetracycline concentrations ranging from 30 µg/ml down to 30 ng/ml are routinely detected (FIG. 5). Thus as little as 300 pg of tetracycline is routinely detected, and sometimes as little as 100 pg of tetracycline is detected.

Alternatively, a liquid assay is also used. Cells are grown in LB (pH 7.5), and tetracycline-containing samples are added to aliquots when the density of the culture is 0.1 OD units. After 3–4 generations of the cells, each aliquot is measured for β-galactosidase activity as described (10, 12) and Miller Units (12) are determined. In liquid assays, as little as 0.1 ng/ml of tetracycline could be detected, and 5–10 ng/ml resulted in full induction (FIG. 6), in keeping with previous results reported by Bertrand, et al. (9). For both the plate and liquid assays, this strain is more sensitive than a previously reported screening organism (11).

Either the plate assay or the liquid assay is capable of detecting all tetracyclines previously known to have antibacterial activity. These compounds include tetracycline, chlortetracycline, minocycline, doxycycline, 6-dimethyl chlortetracycline, and 6-deoxy-6-dimethyl tetracycline. Anhydro derivatives of tetracycline can also be detected, consistent with previous results (11).

A variety of other antibiotics are tested for activity with the plate assay to test whether other antibiotics result in a positive signal. Table 2 shows that several compounds, when in discs that were placed on an assay plate, result in the production of purple color to a limited extent. The amount of nonspecific drug resulting in a positive signal, however, is 3 orders of magnitude higher than the amount of tetracycline needed for induction. A purple ring is detectable only when high concentrations of the nonspecific drugs are applied, surrounding a prominent zone of growth inhibition. It is possible that the thin purple ring surrounding a large growth inhibitory zone might be an artifact, for example, of permeabilizing the cells to calorimetric reagent; it is interesting that members of the β-lactam class of antibiotics sometimes cause this response. In any case, it is clear that the assay organism discriminates very well for tetracyclines, yet is sensitive to a wide variety of tetracycline structures. To reinforce this result, a second set of experiments is conducted by applying multiple 2–3 µl samples containing approximately 250 ng of a given drug onto an assay plate (Table 3). None of a variety of drugs tested results in a positive response.

TABLE 2

Response of the Tetracycline and Inhibition Assays

| Compound | Induction Assay | Inhibition Assay |
|---|---|---|
| Amikacin 30 µg | − | − |
| Ampicillin 10 µg | + | + |
| Azlocillin 30 µg | nt | − |
| Aztreonam 30 µg | − | − |
| Bacitracin 10 U | − | − |
| Carbenicillin 100 µg | + | + |
| Cefamandole 30 µg | ± | + |
| Cefsulodin 30 µg | nt | ± |
| Cefoxitin 30 µg | nt | + |
| Cefotaxime 30 µg | + | nt |
| Ceftazidine 30 µg | ++ | ++ |
| Cephaleridine 30 µg | nt | + |
| Cephalethin 30 µg | + | + |
| Chloremphenicol 30 µg | − | − |
| Cinoxacin 100 µg | ± | − |
| Clindamycin 2 µg | − | − |
| Cloxacillin 5 µg | nt | − |
| Colistin 10 µg | − | − |
| Erythromycin 15 µg | − | − |
| Ethidium bromide 10 µg | nt | − |
| Gentamicin 10 µg | − | − |
| Imipenem 10 µg | ++ | ++ |
| Kanamycin 30 µg | − | − |
| Methicillin 5 µg | − | − |
| Mitomycin 10 µg | − | − |
| Moxalactam 30 µg | − | + |
| Nalidixic Acid 30 µg | − | − |
| Nafcillin 1 µg | − | − |
| Neomycin 5 µg | − | nt |
| Norfloxacin 10 µg | − | − |
| Novobiocin 30 µg | − | − |
| Nystatin 100 U | ++ | − |
| Oxacillin 1 µg | − | − |
| Penicillin G 10 U | − | − |
| Piperacillin 100 µg | ± | − |
| Polymyxin B 300 U | − | − |
| Rifampin 5 µg | − | − |
| Streptomycin 10 µg | − | − |
| Sulfachloropyridazine 1 mg | − | − |
| Sulfadiazine 300 µg | − | − |
| Sulfamethizole 250 µg | − | − |
| Sulfathiazole 300 µg | − | − |
| Ticarcillin 75 µg | + | + |
| Ticarcillin + Clavulinic Acid | ± | ± |
| Tobramycin 10 µg | − | − |
| Trimetheprim-Sulfamethoxazole | − | − |

TABLE 2-continued

Response of the Tetracycline and Inhibition Assays

| Compound | Induction Assay | Inhibition Assay |
|---|---|---|
| Vancomycin 30 µg | ± | – |
| Tetracycline Detection | ≧300 pg | ≧1 ng |

Notes:
nt Not tested
± Possible positive
+ Weak positive
++ Stronger positive
– Negative

TABLE 3

Compounds Tested in the
Tetracycline, Inhibition and Synergy Assays

| Class of Antibiotic | Antibiotic Name |
|---|---|
| Unknown | Antibiotic A1531 |
| Unknown | Antibiotic A4825 |
| Unknown | Antibiotic A7363 |
| Unknown | Antibiotic 9537 |
| Unknown | Antibiotic AM374 #22 |
|  | Monazomycin |
| Actinomycin | Actinomycin Crude |
| Aminoglycoside | Antibiotic AM31 beta and gamma |
| Aminoglycoside | Antibiotic BM123, Alba, SO4 |
| Aminoglycoside | Antibiotic BM782 |
| Aminoglycoside | Paromomycin sulfate |
| Ansamycin | Geldamycin |
| Antifungal | Antiprotozoin |
| Aurodox type | Antibiotic C08078 Alpha |
| Basic macrolide | Leucomycin |
| Basic macrolide | Relomycin, LL-AM684 beta |
| Beta lactam | penicillin N crude |
| Chloramphenical | Chloramphenical |
| Cyclic depsipeptide | Antibiotic A0341 Beta, hydrochloride |
| Cyclic depsipeptide | Etamycin, Na salt |
| Cyclic depsipeptide | valinomycin/miticide |
| Cyclic peptide | Bacitracin |
| Cyclic peptide | Nonactin (AE409 Gamma) |
| Cyclic peptide | Polymyxin-B-SO4 |
| Fungal metabolite | Antibiotic V214X |
| Fungal metabolite | Antibiotic V241 W |
| Fungal metabolite | Antibiotic Z-1220A #3 |
| Fungal metabolite | Clavacin/patulin |
| Fungal metabolite | Fusarinic Acid |
| Fungal metabolite | Gliotoxin |
| Glycopeptide | Avoparcin sulfate |
| Glycospermidine | Antibiotic BM123 Gamma, HCl |
| Hygromycin A | Hygromycin A |
| Lincomycin | Lincomycin HCl |
| Lipopeptide | Aspartocin, Na salt |
| Macrolide | Neutramcin |
| Miscellaneous | Actithzic acid/mycobacidin |
| Miscellaneous | Alasopeptin |
| Miscellaneous | Citrinin |
| Miscellaneous | Usnic Acid |
| Naphthoquinone | Frenolicin (AC860 alpha) |
| Netropsin | Netropsin, HCl |
| Nucleoside | Angustamycin |
| Nucleoside | Blasticidin "S" |
| Nucleoside | Nucleocidin |
| Nucleoside | Puromycin Aminonucleoside |
| Nucleoside | Puromycin HCl |
| Orthosomycins | Avilamycin |
| Phenazine | Phenazine Alpha-COOH |
| Plant hormone | Gibberellic Acid |
| Polyene | Nystatin |
| Polyether | Antibiotic BL580 Alpha |
| Quinocycline | Isoquinocycline HCl (AA575 Gamma) |
| Quinomycin type | Levomycin |
| Streptothricin type | Antibiotic AC541, sulfate |

TABLE 3-continued

Compounds Tested in the
Tetracycline, Inhibition and Synergy Assays

| Class of Antibiotic | Antibiotic Name |
|---|---|
| Aracil-peptide | Antibiotic B02964 complex |
| Viomycin | Viomycin, sulfate |
| Virginiamycin type | Streptogramin/vertimycin |

Approximately 250 ng of the indicated drug was spotted onto each assay plate. None of these drugs tested positive for the Tetracycline, Inhibition, or Synergy Assays.

A variety of strains known to produce tetracyclines, from the Lederle collection, are grown to stationary phase. All routinely test positive in the plate assay, including the original Duggar isolate, strain A377, that produces a low level of chlortetracycline. When assaying unknown cultures to detect tetracycline producers, the original Duggar strain is grown using the identical growth regimen and is tested as a positive control. In addition, fermentation broths of unknown cultures isolated from soil are identified as producers of tetracycline derivatives.

Construction of tet-Resistant Screening Microorganisms

A derivative plasmid pBT401 (9) containing tetA gene of transposon Tn10 is constructed by digesting plasmid pCB-Sal with SmaI restriction enzyme and ligating the small fragment into plasmid pBT401 digested with BamHI enzyme and filled in with Klenow enzyme as described (8). In the construct that confers tetracycline resistance, the gene is in the same orientation as the kanamycin resistance gene, determined by restriction analysis. When the gene is in the opposite orientation, no tetracycline resistance is detected. It is possible that readthrough transcription past the kanamycin resistance gene accounts for the low level of expression of the tetA gene. An isogenic plasmid containing the tetK gene of S. aureus is similarly constructed using plasmid pGG57, described above, as the source of tetK. Both of these plasmids are transformed into the derivative of strain NK5031 containing the hybrid λ phage described. Strain KB4 contains tetA. Strain KBS contains tetK.

FIG. 7 shows a comparison of induction observed with KB3ind, KB4, and KB5. KB3ind is tetracycline-sensitive, and induces maximally at just 5–10 ng/ml of tetracycline. KB4, which contains the tetA gene, confers resistance to less than 10 µg/ml, in comparison with a Tn10 derivative of KB3ind which is resistant to more than 100 µg/ml of tetracycline. KB4 prevents induction in the presence of 5 ng/ml more effectively than the Tn10 strain, probably because of its constitutive expressions. Thus, more pumps may be synthesized when strain KB4 is exposed to very low concentrations of tetracycline. This results in a reduction of the internal concentration of tetracycline and little induction compared with the Tn10 strain. However, when tetracycline concentrations are increased only slightly, strain KB4 cannot respond by making more efflux pumps, and full induction occurs when the concentration of tetracycline is increased to 30 ng/ml. The Tn10 strain requires 1 µg/ml of tetracycline for full induction. Thus, strain KB4 appears to be close to the optimum in terms of detecting inhibitors of the tetracycline efflux pump, in the sense that inhibition of very few pumps may result in a response.

Strain KB5 is isogenic to strain KB4, except the tetK gene confers a low level of tetracycline resistance. The MIC of strain KB5 is also about 10 µg/ml of tetracycline. The tetK gene results in a similar shift in the induction curve compared to strain KB4. Both strains grow in the presence of 5 µg/ml of tetracycline, albeit slower than in the absence of tetracycline.

Assays for Efflux Pump Inhibitors

Two assays are developed for detecting inhibitors of the tetA gene product (using strain KB5), or the tetK gene product (using strain KB4). In the Inhibition Assay, cells of strain KB4 or KB5 are treated as described in the tetracycline screen above, except that the agar medium contains 5 ng/ml of tetracycline. Alternatively a Liquid Assay is also developed. Cells are first grown in LB (pH 7.5). Then cells are shifted to medium containing 5 ng/ml of tetracycline, and tetracycline-containing samples are added to aliquots. Cells are then incubated and assayed as described for the Tetracycline Assay. The Inhibition Assay relies on the fact that full induction of tetA occurs in the presence of 5–10 ng/ml of tetracycline in strain KB3ind (FIG. 7). However, the intracellular concentration is reduced in tetracycline resistant strains due to the action of the efflux pump, so more tetracycline would be required in the medium to accumulate sufficient tetracycline inside the cell to induce. The Inhibition Assay is designed to detect compounds that cause β-galactosidase induction in the presence of sub-inducing levels of tetracycline for a resistant strain.

In the Synergy Assay, cells are treated as above for the plate assay, except that agar medium contains 5 µg/ml of tetracycline, near the MIC for strain KB4 or KB5. Growth inhibition is detected by the lack of purple color production following the overlay containing a calorimetric reagent. Alternatively, cells are treated as above for the liquid assay, except that cells are shifted to medium containing 5 µg/ml of tetracycline. This screen is designed to detect compounds, antibiotics, fermentation broths, etc. that kill the assay organism in combination with tetracycline, i.e. to detect substances that cause growth inhibition in the presence of 5 µg/ml of tetracycline, but not in the absence of tetracycline.

The ideal compound is one which causes growth inhibition in the Synergy Assay, and induction in the Inhibition Assay.

There are no available positive controls that are known to be efflux pump inhibitors. The lipophilic chelating agents, such as fusaric acid, designed to kill cells expressing the efflux pump in either the presence or absence of tetracycline (20) do not test positive in the Inhibition or Synergy Assays using strain KB4. These agents are only active when cells strongly express the pump, at low cell density, and in special medium. Some fermentation broths, however, contain material that test positive in both the Inhibition and Synergy plate assays (FIG. 8). The predominant active component produced by one bacterial culture is found to be nocardamine, a siderophore which binds Fe+++, for both strains KB4 and KB5. One µg of nocardamine is sufficient to detect activity in the Synergy Assay or the Inhibition Assay. To test whether nocardamine uniquely antagonizes the pump, or whether other iron-binding compounds also have the same effect, the siderophores ferrichrome and ferrichromeA are also tested for their ability to antagonize the tetracycline efflux pump. Both compounds test positive at the same molar concentrations as nocardamine. Only the unchelated forms of that iron chelators exhibit this inhibitory activity.

The effect of nocardamine can be detected in liquid assays, as shown in FIG. 9. Cells grown in liquid culture in the presence of 5 ng/ml only induce β-galactosidase at a low level; however, when nocardamine is also present at concentrations greater than 5 µg/ml, then a rise in β-galactosidase occurs, for either strain KB4 or KB5. When cells are growing in the presence of 5 µg/ml, then growth inhibition, detected most clearly by the inhibition of β-galactosidase production, is apparent for both strains.

FIG. 10 shows that when the Tn10 derivative of strain KB3ind (a highly resistant strain) is grown in the presence of 25 µg/ml of tetracycline, then nocardamine inhibits growth of the TN10 strain, whereas nocardamine has little or no effect when tetracycline is absent. Thus, nocardamine and other siderophores have the effect of interfering with the ability of the pump to maintain low levels of tetracycline inside cells.

Table 2 shows that when a variety of antibiotics are tested on plate assays, few cause a positive response in the Inhibition Assay, and none in the Synergy Assay. One notable exception for the Inhibition Assay are tetracycline derivatives, which cause induction when as little as 1 ng is spotted in the plate assay for both strain KB4 or KB5. When tetracycline is spotted on the assay plate, then the efflux pump cannot pump out sufficient tetracycline to prevent induction. Therefore the Inhibition Assay should be run in conjunction with the Tetracycline Assay, which will show a stronger positive response to tetracycline. The same β-lactam antibiotics that cause a purple ring surrounding a large zone of growth inhibition in the Tetracycline Assay (Table 1) shows a similar response in the Inhibit Assay as well. Nocardamine, in contrast, shows no response in the Tetracycline Assay, shown in FIG. 10, even though it is detected in both the Inhibition and Synergy Assays.

Screening Fermentation Broths

The most prevalant components in fermentation broths that cause a positive response are siderophores. Fortunately, CAS plates (21) provide a reliable test for siderophores, so that these active materials can be identified quickly.

In summary, three screens are provided that can be run in conjunction. The Tetracycline Assay is designed to detect pg levels of tetracyclines. The Inhibition Assay can detect 1 ng of tetracycline. The Inhibition and Synergy Assays are designed to detect compounds such as nocardamine, which interfere with the ability of the tetracycline efflux pumps from maintaining a low intracellular level of tetracycline. Nocardamine also inhibits the growth of a fully tetracycline-resistant strain in combination with 25 µg/ml of tetracycline. It is apparently the chelating ability of nocardamine that is responsible for its activity, since other strong iron chelators have a similar effect. While not wishing to be bound by any theory, it is possible that nocardamine, by binding iron, causes a state of iron deprivation that interferes with functions that depend on oxidative-reduction reactions. It is noteworthy that active efflux of tetracycline is energized by the protein gradient, which depends on electron transport, and iron, to maintain the full proton motive force, providing a plausible explanation of the connection between iron-free siderophores and the interference with the efflux pumps. However, it is also possible that treatment with nocardamine enhances the uptake of tetracycline with the cell, since the tetracycline sensitive strain KB3ind is affected by the combination of tetracycline and nocardamine. It is possible that enhancing the uptake of tetracycline into cell containing tetracycline efflux pumps is an alternative means of antagonizing these pumps.

The following biological materials have been deposited with the American Type Culture Collection, 12301 Parklawn Drive, Rockville, Md., on Dec. 3, 1991, and have been given the designated accession numbers. These are also available in the culture collection of American Cyanamid Company, Lederle Laboratories, Pearl River, N.Y.

| Plasmid | Accession No. |
|---|---|
| E. coli MC1061/pCBSal | ATCC 68855 |
| E. coli MC1061/pGG57 | ATCC 68856 |
| E. coli KB3ind | ATCC 68857 |
| E. coli KD4 | ATCC 68858 |
| E. coli KB5 | ATCC 68859 |

BIBLIOGRAPHY

1. McMurray, L. M., R. E. Petrucci, Jr., and S. B. Levy. 1980. Active efflux of tetracycline encoded by four genetically different tetracycline resistance elements in *Escherichia coli*. Proc. Natl. Acad. Sci. 77:3974–3977.
2. Mojumdar, M. and S. A. Khar. 1988. Characterization of the tetracycline resistance gene of plasmid pT181 of *Staphylococcus aureus*. J. Bacteriol. 170:5522–5528
3. Coleman, D. C., and T. J. Foster. 1981. Analysis of the reduction in expression of tetracycline resistance determined by transposon Tn10 in the multicopy state. Mol. Gen. Genet. 182171–177.
4. Moyed, J. S., T. T. Nguyen, and K. P. Bertrand. 1983. Multicopy Tn10 tet plasmids confer sensitivity to induction of tet gene expression. J. Bacteriol. 155:549–556.
5. Bertrand, K. P., K. Postle, L. V. Wray, Jr., and W. S. Reznikoff. 1983. Overlapping divergent promoters control expression of Tn10 tetracycline resistance. Gene. 23:149–156.
6. Hillen, W., K. Schollmeier, and C. Gatz. 1984. Control of expression of the Tn10-encoded tetracycline resistance operon II. Interaction of RNA polymerase and TET repressor with the tet operon regulatory region. J. Mol. Biol. 172185–201.
7. Eckert, B., and C. F. Beck. 1989. Overproduction of Transposon Tn10-Encoded Tetracycline Protein Results in Cell Death and Loss of Membrane Potential. J. Bact. 171:3557–3559.
8. Sambrook, J., E. F. Fritsch and T. Maniatis. 1989. Molecular Cloning; a laboratory manual (second edition). Cold Spring Harbor Laboratory Press, Cold Spring Harbor, N.Y.
9. Bertrand, K. P., K. Postle, L. V. Wray, Jr., and W. S. Resnikoff. 1984. Construction of a single-cop promoter vector and its use in analysis of regulation of the transposon Tn10 tetracycline resistance determinant. J. Bacteriol. 158:910–919.
10. Miller, J. H. 1972. Experiments in Molecular Genetics. Cold Spring Harbor Laboratories, Cold Spring Harbor, N.Y.
11. Chopra, I., K. Hacker, Z. Misulovin and D. M. Rothstein. 1990. Sensitive biological detection method for tetracycline using a tetA-lacZ fusion system. Antimicrob. Agents Chemoth. 34:111–116.
12. Rothstein, D. M., G. Pahel, B. Tyler, and B. Magasanik. 1980. Regulation of expression from the glnA promoter of *Escherichia coli* in the absence of glutamine synthetase. Proc. Nat. Acad. Sci. 77:7372–7376.
13. Hershey, A. D. (ed.) 1971. "The Bacteriophage Lamdda". (Cold Spring Harbor Laboratories, Cold Spring Harbor, N.Y.) pp. 31–32.
14. Richard Novick, personal communication.
15. Kunkel, T. A., J. D. Roberts and R. A. Zakour. 1987. Rapid and efficient site-specific mutagenesis without phenotypic selection. Methods Enzymology. 154:367.
16. S. Adya, personal communication.
17. Davis, R. W., D. Botstein, and J. R. Rogh. 1980. *Advanced Bacterial Genetics*. (Cold Spring Harbor Laboratory, Cold Spring Harbor, N.Y.
18. Osburne, M. O., W. M. Maiese, and M. Greenstein. 1990. In vivo inhibition of bacterial DNA gyrase by cinodine, a glycocinnamoylspermidine antibiotic. Antimicrobial Agents and Chemotherapy. 34:1450–1452.
19. Smith, L. D. and K. P. Bertrand. 1988. Mutations in the Tn10 repressor that interfere with induction, location of the tetracycline-binding domain. J. Mol. Biol. 203:949–959.
20. Bochner, B. R., H.-C. Hucang, G. L. Schieven, and B. N. Ames. 1980 Positive selection for loss of tetracycline resistance. J. Bacterial. 143:926–933.
21. Schwyn, B. and J. B. Netlands. 1987. Universal chemical assay for the detection and determination of siderophores. Analytical Biochemistry 160:47–56.
22. Gold, L. and G. Stormo. 1987. *Eschericia coli* and Salmonella Typhimurium: Cellular and Molecular Biology. F. C. Niedhard (ed.) American Society of Microbiology. Washington, D.C. Vol. 2:1302–1307.

What we claim is:

1. A microorganism which comprises:

(a) an indicator gene fused to a tetA promoter, the gene present in a single copy or low copy number;

(b) a tetR gene expressed at a level sufficient to inhibit expression of the indicator gene of (a); and (c) a constitutively expressed gene encoding a tetracycline efflux pump, wherein the constitutively expressed gene is removed from the influence of its native promoter.

2. The microorganism of claim 1, wherein the indicator gene fused to a tetA promoter is present in a single copy number.

3. The microorganism of claim 1, wherein the tetR gene is expressed at a level producing sensitivity to 10 ng or less of tetracycline.

4. The microorganism of claim 1, wherein the tetR gene is present without its transcriptional start signal.

5. The microorganism of claim 1, wherein the constitutively expressed gene encoding a tetracycline efflux pump is tetA.

6. The microorganism of claim 1, wherein the constitutively expressed gene encoding a tetracycline efflux pump is tetK.

7. A method for detecting a tetracycline efflux pump inhibitor in a test sample, the method comprising the steps of:

(a) contacting the microorganism of claim 1, in the presence of sub-inhibitory but inducing levels of tetracycline, with the sample to be tested and a reagent which produces a detectable signal when the indicator gene is expressed; and (b) observing the presence or absence of a detectable signal in the microorganism of (a), wherein the absence of a detectable signal indicates the presence of a tetracycline efflux pump inhibitor in the sample.

8. The method of claim 7, wherein the microorganism is capable of growth at 37° C.

9. The method of claim 7, wherein the indicator gene is lacZ.

10. The method of claim 7, wherein the tetR gene is expressed at a level producing sensitivity to 10 ng of less or tetracycline.

11. The method of claim 7, wherein the microorganism further comprises a mutant allele of the CI gene.

12. The method of claim 11, in which the reagent producing the detectable signal is 6-bromo-2-naphthyl-β-D-galactopyranoside and Fast Blue RR.

13. The method of claim 7, wherein the constitutively expressed gene encoding a tetracycline efflux pump is tetA.

14. The method of claim 13, wherein the microorganism is KB4.

15. The method of claim 7, wherein the constitutively expressed gene encoding a tetracycline efflux pump is tetK.

16. The method of claim 15, wherein the microorganism is KB5.

17. A method for detecting a tetracycline efflux pump inhibitor in a test sample, the method comprising the steps of:

(a) contacting the microorganism of claim 1, in the presence of non-inhibitory and sub-inducing levels of tetracycline, with the sample to be tested and a reagent which produces a detectable signal when the indicator gene is expressed; and (b) observing the presence or absence of a detectable signal in the microorganism of (a), wherein the absence of a detectable signal indicates the presence of a tetracycline efflux pump inhibitor in the sample.

18. The method of claim 17, wherein the microorganism is capable of growth at 37° C.

19. The method of claim 17, wherein the indicator gene is lacZ.

20. The method of claim 17, wherein the tetR gene is expressed at a level producing sensitivity to 10 ng or less of tetracycline.

21. The method of claim 17, wherein the microorganism further comprises a mutant allele of the CI gene.

22. The method of claim 21, in which the reagent producing the detectable signal is 6-bromo-2-naphthyl-β-D-galactopyranoside and Fast Blue RR.

23. The method of claim 17, wherein the constitutively expressed gene encoding a tetracycline efflux pump is tetA.

24. The method of claim 23, wherein the microorganism is KB4.

25. The method of claim 17, wherein the constitutively expressed gene encoding a tetracycline efflux pump is tetK.

26. The method of claim 25, wherein the microorganism is KB5.

* * * * *

UNITED STATES PATENT AND TRADEMARK OFFICE
CERTIFICATE OF CORRECTION

PATENT NO.    : 5,789,188
DATED         : May 13, 1996
INVENTOR(S)   : David M. Rothstein, Gorday G. Guay It is certified that error appears in the above-identified patent and that said Letters Patent is hereby corrected as shown below:

<u>Column 28,</u>
Line 19, "absence" should read -- "presence" --

Signed and Sealed this

Eighteenth Day of September, 2001

Attest:

*Nicholas P. Godici*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GTTGACACTC TATCATTGAT AGAGTTATTT TACCACTCCC TATCAGTGAT AGAGAAAAGT      60
GAAATG                                                                 66
```

( 2 ) INFORMATION FOR SEQ ID NO:2:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGATCCATAG AGAAAGTCGA CATGAACTCG AGTACAAAGA TCGCATTGGT AATTACGTTA    60

CTCGATGCCA TGG                                                       73
```

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GGATCCATAG AGAAAGTCGA CATGTTTAGT TT                                  32
```

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GGATCCATAG AGAAAGTCGA CTTGTTTAGT TT                                  32
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GTAAAGAGGT AAAATTGTTT AGTTTA                                         26
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GTCGACATGT TTAGTTT                                                   17
```

( 2 ) INFORMATION FOR SEQ ID NO:7:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

```
GTCGACTTGT TTAGTTT                                                      17
```

( 2 ) INFORMATION FOR SEQ ID NO:8:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
GATCCATAGA GAAAAGTCGA CATGAACTCG AGTACAAAGA TCGCATTGGT AATTACGTTA        60
CTCGATGC                                                                68
```

( 2 ) INFORMATION FOR SEQ ID NO:9:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GTATCTCTTT CAGCTGTACT TGAGCTCATG TTTCTAGCGT AACCATTAAT GCAATGAGCT        60
ACGGTAC                                                                 67
```

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CCTCAAGTAA AGAGGTCGAC ATGTTAGTTT AG                                     32
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
AAGAGGTCGA CTTGTTTAGT TAAG                                              24
```